United States Patent
Xu et al.

(10) Patent No.: US 11,352,603 B2
(45) Date of Patent: *Jun. 7, 2022

(54) METHODS FOR IN VITRO MEMORY B CELL DIFFERENTIATION AND TRANSDUCTION WITH VSV-G PSEUDOTYPED VIRAL VECTORS

(71) Applicant: IMMUSOFT CORPORATION, Seattle, WA (US)

(72) Inventors: Mei Xu, Seattle, WA (US); Matthew Rein Scholz, Seattle, WA (US); Eric J. Herbig, Seattle, WA (US)

(73) Assignee: Immusoft Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/267,150

(22) Filed: Feb. 4, 2019

(65) Prior Publication Data

US 2019/0241870 A1    Aug. 8, 2019

Related U.S. Application Data

(63) Continuation of application No. 14/776,283, filed as application No. PCT/US2014/027910 on Mar. 14, 2014, now Pat. No. 10,240,125.

(60) Provisional application No. 61/785,490, filed on Mar. 14, 2013.

(51) Int. Cl.
| | |
|---|---|
| *C12N 15/86* | (2006.01) |
| *C12N 5/00* | (2006.01) |
| *C12N 5/0781* | (2010.01) |
| *A61K 48/00* | (2006.01) |

(52) U.S. Cl.
CPC ...... *C12N 5/0635* (2013.01); *C12N 2501/231* (2013.01); *C12N 2501/2302* (2013.01); *C12N 2501/2306* (2013.01); *C12N 2501/2315* (2013.01); *C12N 2501/24* (2013.01); *C12N 2501/52* (2013.01); *C12N 2510/02* (2013.01)

(58) Field of Classification Search
CPC .......... C12N 5/0635; C12N 2501/2302; C12N 2501/2306; C12N 2501/231; C12N 2501/2315; C12N 2501/24; C12N 2501/52; C12N 2510/02
See application file for complete search history.

(56) References Cited

U.S. PATENT DOCUMENTS

| | | | |
|---|---|---|---|
| 4,937,190 A | 6/1990 | Palmenberg et al. | |
| 5,057,423 A | 10/1991 | Hiserodt et al. | |
| 5,124,259 A | 6/1992 | Tada | |
| 5,283,185 A | 2/1994 | Epand et al. | |
| 5,297,983 A | 3/1994 | Mueller et al. | |
| 5,420,032 A | 5/1995 | Marshall et al. | |
| 5,626,561 A | 5/1997 | Butler et al. | |
| 5,661,018 A | 8/1997 | Ashley et al. | |
| 5,787,900 A | 8/1998 | Butler et al. | |
| 5,843,069 A | 12/1998 | Butler et al. | |
| 5,902,745 A | 5/1999 | Butler et al. | |
| 5,913,998 A | 6/1999 | Butler et al. | |
| 5,980,889 A | 11/1999 | Butler et al. | |
| 6,013,516 A | 1/2000 | Verma et al. | |
| 6,218,181 B1 | 4/2001 | Verma et al. | |
| 6,423,498 B1 | 7/2002 | Markland et al. | |
| 6,833,252 B1 | 12/2004 | Dujon et al. | |
| 6,878,548 B2 | 4/2005 | Tokudome et al. | |
| 7,084,105 B2 | 8/2006 | Chakrabarty et al. | |
| 7,301,010 B2 | 11/2007 | Chakrabarty et al. | |
| 7,338,766 B2 | 3/2008 | Chakrabarty et al. | |
| 7,381,701 B2 | 6/2008 | Chakrabarty et al. | |
| 7,491,394 B2 | 2/2009 | Chakrabarty et al. | |
| 7,511,117 B2 | 3/2009 | Chakrabarty et al. | |
| 7,556,810 B2 | 7/2009 | Chakrabarty et al. | |
| 7,799,555 B2 | 9/2010 | Ragsdale et al. | |
| 7,887,793 B2 | 2/2011 | Tremblay et al. | |
| 8,551,780 B2 | 10/2013 | Agrawal et al. | |
| 8,633,029 B2 | 1/2014 | Akada et al. | |
| 9,074,223 B2 | 7/2015 | Schotz et al. | |
| 10,240,125 B2 * | 3/2019 | Xu et al. | |
| 2003/0115614 A1 | 6/2003 | Kanda et al. | |
| 2003/0232410 A1 | 12/2003 | Liljedahl et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2006/0063231 A1 | 3/2006 | Li et al. | |
| 2006/0188987 A1 | 8/2006 | Guschin et al. | |
| 2007/0065431 A1 | 3/2007 | Coia et al. | |
| 2007/0117128 A1 | 5/2007 | Smith et al. | |
| 2008/0188431 A1 | 8/2008 | Chiorini et al. | |

(Continued)

FOREIGN PATENT DOCUMENTS

| | | |
|---|---|---|
| EP | 0350641 A2 | 1/1990 |
| WO | WO 2006/072620 A1 | 7/2006 |

(Continued)

OTHER PUBLICATIONS

Lefevre et al. Interferon-delta: the first member of a novel type I interferon family. Biochimie 80:779-788, (Year: 1998).*
Frecha et al. Advances in the field of lentivector-based transduction of T and B lymphocytes for gene therapy. Molecular Therapy 18:1748-1757, (Year: 2010).*
Serafini et al. Molecular evidence of inefficient transduction of proliferating human B lymphocytes by VSV-pseudotyped HIV-1-derived lentivectors. Virology 325:413-424, (Year: 2004).*
Kvell et al. Transduction of CpG DNA-stimulated primary human B cells with bicistronic lentivectors. Molecular Therapy 12:892-899, (Year: 2005).*

(Continued)

*Primary Examiner* — Quang Nguyen
(74) *Attorney, Agent, or Firm* — Cooley LLP

(57) ABSTRACT

The present disclosure relates to the in vitro differentiation of memory B cells to plasmablasts or plasma cells and genetic modification of these cells to express a protein of interest, such as a specific antibody or other protein therapeutic.

18 Claims, 5 Drawing Sheets

(56) References Cited

U.S. PATENT DOCUMENTS

| | | | |
|---|---|---|---|
| 2009/0117617 | A1 | 5/2009 | Holmes et al. |
| 2009/0220998 | A1 | 9/2009 | Hsu et al. |
| 2009/0263900 | A1 | 10/2009 | DeKelver et al. |
| 2010/0047805 | A1 | 2/2010 | Wang |
| 2010/0113745 | A1 | 5/2010 | Spits et al. |
| 2010/0203630 | A1 | 8/2010 | Luo et al. |
| 2011/0207221 | A1 | 8/2011 | Cost et al. |
| 2011/0301073 | A1 | 12/2011 | Gregory et al. |
| 2013/0084637 | A1 | 4/2013 | Endl et al. |
| 2013/0143267 | A1 | 6/2013 | Scholz et al. |
| 2014/0349397 | A1 | 11/2014 | Thomson et al. |
| 2014/0363411 | A1 | 12/2014 | Eisenbach-Schwartz et al. |
| 2016/0046908 | A1 | 2/2016 | Xu et al. |
| 2016/0083440 | A1 | 3/2016 | Mineau |
| 2016/0256526 | A1 | 9/2016 | Kumar et al. |
| 2018/0002664 | A1 | 1/2018 | Scholz et al. |
| 2021/0047619 | A1 | 2/2021 | Scholz et al. |

FOREIGN PATENT DOCUMENTS

| | | | | |
|---|---|---|---|---|
| WO | WO 2006/095164 | A1 | | 9/2006 |
| WO | WO 2007/014275 | A2 | | 2/2007 |
| WO | WO 2007/098934 | A1 | | 9/2007 |
| WO | WO 2010/059876 | A2 | | 5/2010 |
| WO | WO 2011/085247 | | * | 7/2011 |
| WO | WO 2014/152832 | A1 | | 9/2014 |
| WO | WO 2016/057975 | A2 | | 4/2016 |
| WO | WO 2016/100932 | A1 | | 6/2016 |
| WO | WO 2016/161446 | A1 | | 10/2016 |
| WO | WO 2016/187017 | A1 | | 10/2016 |
| WO | WO 2019/178613 | A1 | | 9/2019 |

OTHER PUBLICATIONS

Jourdan et al. An in vitro model of differentiation of memory B cells into plasmablasts and plasma cells including detailed phenotypic and molecular characterization. Blood 114:5173-5181, (Year: 2009).*

Chinnasamy et al. Lentiviral-mediated gene transfer into human lymphocytes: role of HIV-1 accessory proteins. Blood 96:1309-1316, (Year: 2000).*

Mock et al. Efficient lentiviral transduction and transgene expression in primary B cells. Human gene therapy methods 23:408-415, ( Year: 2012).*

Janssens et al. Efficiency of onco-retroviral and lentiviral gene transfer into primary mouse and human B-lymphocytes is pseudotype dependent. Human gene therapy 14:263-276, (Year: 2003).*

Bovia et al. Efficient transduction of primary human B lymphocytes and nondividing myeloma B cells with HIV-1-derived lentiviral vectors. Blood 101:1727-1733, (Year: 2003).*

Adra, C.N., et al., "Cloning and expression of the mouse pgk-1 gene and the nucleotide sequence of its promoter." Gene (1987); 60: 65-74.

Abkowitz, J.L., et al., "Evidence that hematopoiesis may be a stochastic process in vivo." Nature Medicine (1996); 2.2: 190-197.

Akahane, K., et al., "Effects of recombinant human tumor necrosis factor (rhTNF) on normal human and mouse hemopoietic progenitor cells." Int J Cell Cloning (1987); 5(1): 16-26.

Arch et al., "Tumor necrosis factor receptor-associated factors (TRAFs)—a family of adapter proteins that regulates life and death." Genes & Development (1998); 12.18: 2821-2830.

Barbas et al., "Recombinant human Fab fragments neutralize human type 1 immunodeficiency virus in vitro." Proc Natl Acad Sci U S A. (1992); 89(19): 9339-9343.

Bierer et al., "Cyclosporin A and FK506: molecular mechanisms of immunosuppression and probes for transplantation biology." Curr Opin Immunol. (1993); 5: 763-773.

Brown and Attardi, "The role of apoptosis in cancer development and treatment response." Nature Reviews Cancer (2005), 5.3 : 231-237.

Buchholz, C.J., et al., "Lentiviral vectors with measles virus glycoproteins—dream team for gene transfer?." Trends in Biotechnology (2009); 27.5: 259-265.

Buchwald et al., "Long-term, continuous intravenous heparin administration by an implantable infusion pump in ambulatory patients with recurrent venous thrombosis." Surgery (1980); 88(4): 507-516.

Chen et al., "Bifunctional fusion proteins of the human engineered antibody domain m36 with human soluble CD4 are potent inhibitors of diverse HIV-1 isolates." Antiviral Res. (2010); 88(1): 107-115.

Chen et al., "Human domain antibodies to conserved sterically restricted regions on gp120 as exceptionally potent cross-reactive HIV-1 neutralizers." Proc Natl Acad Sci U S A. (2008); 105(44): 17121-17126.

Clark et al., "Design, synthesis and selection of DNA-encoded small-molecule libraries." Nat Chem Biol. (2009); 5(9):647-654. doi:10.1038/nchembio.211. Epub (2009). Erratum in: Nat Chem Biol. (2009); 5(10): 772.

Daridon, C., et al., "Epratuzumab targeting of CD22 affects adhesion molecule expression and migration of B-cells in systemic lupus erythematosus." Arthritis Research and Therapy (2010); 12.6: R204.

Defranco et al., "Frequency of B lymphocytes responsive to anti-immunoglobulin." The Journal of Experimental Medicine (1982), 155.5: 1523-1536.

Deglon et al., "Self-inactivating lentiviral vectors with enhanced transgene expression as potential gene transfer system in Parkinson's disease." Hum Gene Ther. (2000); 11(1): 179-190.

Dobson et al., "Conservation of high efficiency promoter sequences in *Saccharomyces cerevisiae*." Nucleic Acids Res. (1982); 10(8): 2625-2637.

During et al., Controlled release of dopamine from a polymeric brain implant: in vivo characterization. Ann Neurol. (1989); 25(4): 351-356.

European Patent Application No. 14768084.7, Extended European Search Report dated Sep. 14, 2016, 7 pages.

European Patent Application No. 15871244.8, Extended European Search Report dated Jun. 6, 2018, 11 pages.

Evans et al., "Human cord blood CD34+CD38-cell transduction via lentivirus-based gene transfer vectors." Hum Gene Ther. (1999), 10(9): 1479-1489.

Fluckiger et al., "In vitro reconstitution of human B-cell ontogeny: from $CD34^+$ multipotent progenitors to Ig-secreting cells." Blood (1998), 92.12: 4509-4520.

Frecha et al., "Efficient and stable transduction of resting B lymphocytes and primary chronic lymphocyte leukemia cells using measles virus gp displaying lentiviral vectors." Blood (2009), 114(15): 3173-3180.

Frecha et al., "Stable transduction of quiescent T cells without induction of cycle progression by a novel lentiviral vector pseudotyped with measles virus glycoproteins." Blood (2008), 112.13: 4843-4852.

Garvin, A.M. et al., "Structure of the murine lck gene and its rearrangement in a murine lymphoma cell line." Molecular and Cellular Biology (1988); 8.8: 3058-3064.

GenBank Database Accession No. AAB26306.1, Jul. 23, 1993 [obtained Oct. 12, 2016], 2 pages.

GenBank Database Accession No. AAB26315.1, Jul. 23, 1993 [obtained Oct. 12, 2016], 2 pages.

Gluzman, Y., "SV40-transformed simian cells support the replication of early SV40 mutants." Cell (1981); 23(1): 175-182.

Gundersen et al., "Tissue-specific methylation of a CpG island in transgenic mice." Gene (1992); 113(2): 207-214.

Gunning et al., "A human beta-actin expression vector system directs high-level accumulation of antisense transcripts." Proc Natl Acad Sci U S A. (1987); 84(14): 4831-4835.

Hamers-Casterman et al., "Naturally occurring antibodies devoid of light chains." Nature (1993); 363(6428): 446-448.

Hawley et al., "Thrombopoietic potential and serial repopulating ability of murine hematopoietic stem cells constitutively expressing interleukin 11." Proc Natl Acad Sci U S A. (1996); 93(19): 10297-10302.

Henderson et al., "Comparison of the effects of FK-506, cyclosporin A and rapamycin on IL-2 production." Immunology (1991); 73(3): 316-321.

(56) References Cited

OTHER PUBLICATIONS

Hildinger et al., "Membrane-anchored peptide inhibits human immunodeficiency virus entry." J Virol. (2001); 75(6): 3038-3042.
Howard et al., "Intracerebral drug delivery in rats with lesion-induced memory deficits." J Neurosurg. (1989); 71(1): 105-112.
International Patent Application No. PCT/US2014/027910, International Preliminary Report on Patentability dated Sep. 15, 2015, 5 pages.
International Patent Application No. PCT/US2014/027910, International Search Report and Written Opinion dated Jul. 3, 2014, 6 pages.
International Patent Application No. PCT/US2015/066908, International Search Report and Written Opinion dated Mar. 18, 2016, 12 pages.
International Patent Application No. PCT/US2015/066908, International Preliminary Report on Patentability dated Jun. 20, 2017, 12 pages.
Inui, A., et al., "Ghrelin, appetite, and gastric motility: the emerging role of the stomach as an endocrine organ." The FASEB Journal (2004); 18(3): 439-456.
Iwakuma et al., "Self-inactivating lentiviral vectors with U3 and U5 modifications." Virology (1999); 261(1): 120-132.
Jaskelioff et al., "SWI-SNF-mediated nucleosome remodeling: role of histone octamer mobility in the persistence of the remodeled state." Mol Cell Biol. (2000); 20(9): 3058-3068.
Jia et al., "Preclinical pharmacokinetics, metabolism, and toxicity of azurin-p28 (NSC745104) a peptide inhibitor of p53 ubiquitination." Cancer Chemother Pharmacol. (2011); 68(2): 513-524.
Jourdan et al., "Characterization of a Transitional Preplasmablast Population in the Process of Human B Cell to Plasma Cell Differentiation", The Journal of Immunology (2011); 187(8): 3931-3941.
Karasuyama et al., "Autocrine growth and tumorigenicity of interleukin 2-dependent helper T cells transfected with IL-2 gene." J Exp Med. (1989); 169(1): 13-25.
Keller et al., "Overexpression of HOX11 leads to the immortalization of embryonic precursors with both primitive and definitive hematopoietic potential." Blood. (1998), 92(3): 877-887.
Krisky et al., "Development of herpes simplex virus replication-defective multigene vectors for combination gene therapy applications." Gene Ther. (1998); 5(11): 1517-1530.
Kwakkenbos et al., "Generation of stable monoclonal antibody-producing B cell receptor-positive human memory B cells by genetic programming." Nature Medicine (2010); 16.1: 123-128.
Langer, R. "New methods of drug delivery." Science (1990); 249(4976):1527-1533.
Lauer et al., "A prototype transduction tag system (delta LNGFR/NGF) for noninvasive clinical gene therapy monitoring." Cancer Gene Ther. (2000); 7(3): 430-437.
Le et al., "A common RNA structural motif involved in the internal initiation of translation of cellular mRNAs." Nucleic Acids Res. (1997); 25(2): 362-369.
Le et al., "A common structural core in the internal ribosome entry sites of picornavirus, hepatitis C virus, and pestivirus." Virus Genes (1996); 12(2):135-147.
LeBien et al., "Multiparameter flow cytometric analysis of human fetal bone marrow B cells." Leukemia (1990), 4.5: 354-358.
Lei et al., "Tolerance induction via a B-cell delivered gene therapy-based protocol: optimization and role of the Ig scaffold." Cell Immunol. (2005); 235(1): 12-20.
Levy et al., "Inhibition of calcification of bioprosthetic heart valves by local controlled-release diphosphonate." Science (1985); 228(4696): 190-192.
Liu et al., "Calcineurin is a common target of cyclophilin-cyclosporin A and FKBP-FK506 complexes." Cell. (1991); 66(4): 807-815.
Lizée, et al., "Lentivirus Vector-Mediated Expression of Tumor-Associated Epitopes by Human Antigen Presenting Cells." Human Gene Therapy (2004); 15 (4): 393-404.

Loken, M.R., et al., "Flow cytometric characterization of erythroid, lymphoid, and monomyeloid lineages in normal human bone marrow." Flow Cytometry in Hematology (1992): 31-42.
Luo et al., "Engineering human hematopoietic stem/progenitor cells to produce a broadly neutralizing anti-HIV antibody after in vitro maturation to human B lymphocytes." Blood (2009), 113: 1422-1431.
Maurice et al., "Efficient gene transfer into human primary blood lymphocytes by surface-engineered lentiviral vectors that display a T cell-activating polypeptide." Blood (2007), 99: 2342-2350.
Meissner et al., "Development of an inducible pol III transcription system essentially requiring a mutated form of the TATA-binding protein." Nucleic Acids Res. 2001; 29(8): 1672-1682.
Miyoshi et al., "Transduction of human CD34+ cells that mediate long-term engraftment of NOD/SCID mice by HIV vectors." Science. (1999), 283(5402): 682-686.
Miyoshi, et al., "Development of a self-inactivating lentivirus vector." J Virol. (1998); 72(10): 8150-8157.
Naldini et al., "In vivo gene delivery and stable transduction of nondividing cells by a lentiviral vector." Science (1996), 272.5259: 263-267.
Narayan et al., "Biology and pathogenesis of lentiviruses." J Gen Virol. (1989); 70 (Pt 7): 1617-1639.
Nguyen et al., "Heavy-chain antibodies in Camelidae; a case of evolutionary innovation." Immunogenetics (2002); 54(1): 39-47.
Nguyen et al., "The specific variable domain of camel heavy-chain antibodies is encoded in the germline." J Mol Biol. (1998); 275(3): 413-418.
Noelle et al., "Cognate interactions between helper T cells and B cells. V. Reconstitution of T helper cell function using purified plasma membranes from activated Th1 and Th2 T helper cells and lymphokines." The Journal of Immunology (1991), 146.4: 1118-1124.
Nogueiras et al., "Ghrelin: new molecular pathways modulating appetite and adiposity." Obes Facts. (2010); 3(5):285-292.
O'Connor, Brian P., et al. "The rise and fall of long-lived humoral immunity: terminal differentiation of plasma cells in health and disease." Immunological Reviews (2003); 194.1: 61-76.
Ohkawa and Taira, "Control of the functional activity of an antisense RNA by a tetracycline-responsive derivative of the human U6 snRNA promoter." Hum Gene Ther. (2000); 11(4): 577-585.
Paule et al., "Survey and summary: transcription by RNA polymerases I and III." Nucleic Acids Res. (2000); 28(6):1283-1298.
Pfeifer et al., "Gene therapy: promises and problems." Annu Rev Genomics Hum Genet. (2001); 2: 177-211.
Pugliese et al., "Self-antigen-presenting cells expressing diabetes-associated autoantigens exist in both thymus and peripheral lymphoid organs." J Clin Invest. (2001); 107(5): 555-564.
Roben et al., "Recognition properties of a panel of human recombinant Fab fragments to the CD4 binding site of gp120 that show differing abilities to neutralize human immunodeficiency virus type 1." J Virol. (1994); 68(8): 4821-4828.
Rosenberg et al. "Use of tumor-infiltrating lymphocytes and interleukin-2 in the immunotherapy of patients with metastatic melanoma. A preliminary report." N Engl J Med. (1988); 319(25): 1676-1680.
Roux, K.H. et al., "Structural analysis of the nurse shark (new) antigen receptor (NAR): Molecular convergence of NAR and unusual mammalian immunoglobulins." Proc. Natl. Acad. Sci. USA (1998); 95: 11804-11809.
Saudek, "A preliminary trial of the programmable implantable medication system for insulin delivery." N Engl J Med. (1989); 321(9): 574-579.
Schmidlin et al., "New insights into the regulation of human B-cell differentiation." Trends in Immunology (2009), 30.6: 277-285.
Sefton, M.V., "Implantable pumps." Crit Rev Biomed Eng. (1987); 14(3): 201-240.
Singer-Sam et al., "Sequence of the promoter region of the gene for human X-linked 3-phosphoglycerate kinase." Gene. (1984); 32(3): 409-417.
Sutton et al., "Human immunodeficiency virus type 1 vectors efficiently transduce human hematopoietic stem cells." J Virol. (1998), 72(7): 5781-5788.

(56) References Cited

OTHER PUBLICATIONS

Takadera et al., Structure of the two promoters of the human lck gene: differential accumulation of two classes of lck transcripts in T cells. Mol Cell Biol. (1989); 9(5):2173-80.
Uchida et al., "HIV, but not murine leukemia virus, vectors mediate high efficiency gene transfer into freshly isolated G0/G1 human hematopoietic stem cells." Proc Natl Acad Sci U S A. (1998), 95(20): 11939-11944.
Verhoeyen et al., "IL-7 surface-engineered lentiviral vectors promote survival and efficient gene transfer in resting primary T lymphocytes." Blood (2003); 101: 2167-2174.
Weisel, J.W., et al., "A model for fibrinogen: domains and sequence." Science (1985); 230(4732): 1388-1391.
Yee et al., "The regulation of myogenin gene expression during the embryonic development of the mouse." Genes Dev. (1993); 7(7A): 1277-1289.
Zelensky et al., "The C-type lectin-like domain superfamily." FEBS J. (2005); 272(24): 6179-6217.
Zhang et al. "Aubiquitous chromatin opening element (UCOE) confers resistance to DNA methylation-mediated silencing of lentiviral vectors." Mol Ther. (2010); 8(9): 1640-1649.
Zufferey et al., "Woodchuck Hepatitis Virus Posttranscriptional Regulatory Element Enhances Expression of Transgenes Delivered by Retroviral Vectors." J. Virol. (1999); 73(4): 2886-2892.
Zufferey et al., "A Murine Leukemia Virus (MuLV) Long Terminal Repeat Derived from Rhesus Macaques in the Context of a Lentivirus Vector and MuLV gag Sequence Results in High-Level Gene Expression in Human T Lymphocytes." J. Virol. (1999); 74: 3668-3681.
Zufferey et al., "Self-inactivating lentivirus vector for safe and efficient in vivo gene delivery." J Virol. (1998); 72(12): 9873-9880.
Zwick et al., "Molecular features of the broadly neutralizing immunoglobulin G1 b12 required for recognition of human immunodeficiency virus type 1 gp120," J Virol. (2003); 77(10): 5863-5876.
U.S. Appl. No. 15/537,334, filed Jun. 16, 2017.
U.S. Appl. No. 16/607,962, filed Oct. 24, 2019.
U.S. Appl. No. 16/981,618, filed Sep. 16, 2020.
International Search Report and Written Opinion dated Jul. 26, 2018 for International Application No. PCT/US2018/029993, 8 pages.
International Preliminary Report on Patentability dated Oct. 29, 2019 for International Application No. PCT/US2018/029993, 16 pages.
Office Action dated May 18, 2021 for Canadian Application No. 2,906,674, 3 pages.
Extended European Search Report dated Dec. 10, 2020 for European Application No. 18790427.1, 8 pages.
Communication pursuant to Article 94(3) dated Nov. 26, 2020 for European Application No. 15871244.8, 5 pages.
Office Action dated Aug. 2, 2021 for Russian Application No. 2019136194, with English translation, 4 pages.
Office Action dated Sep. 8, 2021 for Russian Application No. 2019136194, with English translation, 9 pages.
International Search Report and Written Opinion dated May 28, 2019 for International Application No. PCT/US2019/022821, 13 pages.
Al-Zaidy, S. A. et al., "Follistatin Gene Therapy Improves Ambulation in Becker Muscular Dystrophy." J Neuromuscul Dis., 2(3):185-192 (2015); doi:10.3233/JND-150083.
Argast, G.M. et al., "I-Ppol and I-CreI homing site sequence degeneracy determined by random mutagenesis and sequential in vitro enrichment," J Mol Biol., 280(3):345-53 (1998); doi:10.1006/jmbi.1998.1886.
Ashworth, J. et al., "Computational redesign of endonuclease DNA binding and cleavage specificity," Nature, 441(7093):656-659 (2006); doi:10.1038/nature04818. NIH Public Access Author Manuscript, 11 pages.
Belfort, M. & Roberts, R. R., "Homing endonucleases: keeping the house in order," Nucleic Acids Res., 25(17):3379-3388 (1997); doi:10.1093/nar/25.17.3379.
Benabdallah, B. F. et al., "Overexpression of follistatin in human myoblasts increases their proliferation and differentiation, and improves the graft success in SCID mice," Cell Transplant, 18:709-718 (2019); doi: 10.3727/096368909X470865.
Bona, C. & Bonilla, F. A., "B Cell Development." In Textbook of Immunology. Second Edition. Martin Soohoo (2 ed.). Boca Raton, FL: CRC Press, 1996; p. 102. ISBN 9783718605965.
Bonas, U. et al., "Genetic and structural characterization of the avirulence gene avrBs3 from *Xanthomonas campestris* pv. *Vesicatoria*," Mol Gen Genet., 218(1):127-136 (1989); doi:10.1007/BF00330575.
Burgess, D. J., "A CRISPR genome-editing tool," Nat Rev Genet., 14(2):80 (2013), 1 page; doi: 10.1038/nrg3409.
Caligaris-Cappio, F. et al., "B Cell Populations: The Multiple Myeloma Model." In Manlio Ferrarini & Federico Caligaris-Cappio (Eds.), Human B Cell Populations. Chemical Immunology. Basel, Karger, 1997; 67:102-113. ISBN 3-8055-6460-0.
Capon, D. J. et al., "Designing CD4 immunoadhesins for AIDS therapy," Nature, 337:525-531 (1989).
Case, S. S. et al., "Stable transduction of quiescent CD34+CD38- human hematopoietic cells by HIV-1-based lentiviral vectors," Proc Natl Acad Sci USA. 96(6):2988-2993 (1999).
Chevalier, B. S. et al., "Design, activity, and structure of a highly specific artificial endonuclease," Mol Cell., 10(4):895-905 (2002); doi:10.1016/s1097-2765(02)00690-1.
Christian, M. et al., "Targeting DNA double-strand breaks with TAL effector nucleases," Genetics, 186(2):757-761 (2010); doi:10.1534/genetics.110.120717.
Chu, G. & Sharp, P. A., "SV40 DNA transfection of cells in suspension: analysis of efficiency of transcription and translation of T-antigen," Gene, 13(2):197-202 (1981); doi: 10.1016/0378-1119(81)90008-1.
Civin, C. I. & Loken, M. R., "Cell Surface Antigens on Human Marrow Cells: Dissection of Hematopoietic Development Using Monoclonal Antibodies and Multiparameter Flow Cytometry," Int'l J Cell Cloning, 5:267-288 (1987).
Cong, L. et al., "Multiplex genome engineering using CRISPR/Cas systems," Science, 339(6121):819-823 (2013); doi:10.1126/science.1231143. HHS Public Access Author Manuscript, 9 pages.
Davis, L. G. et al., "Formaldehydegel for electrophoretic separation of RNA and Northern blot," In Basic Methods in Molecular Biology. Elsevier, 1986; pp. 143-146.
Dujon, B. et al., "Mobile introns: definition of terms and recommended nomenclature," Gene,82(1):115-118 (1989); doi:10.1016/0378-1119(89)90035-8.
Emery, A. E. H., "The muscular dystrophies," Lancet, 359(9307):687-695 (2002); doi:10.1016/S0140-6736(02)07815-7.
Epinat, J.-C. et al., "A novel engineered meganuclease induces homologous recombination in yeast and mammalian cells," Nucleic Acids Res., 31(11):2952-2962 (2003); doi: 10.1093/nar/gkg375.
Fan, L. et al., "Improved artificial death switches based on caspases and FADD," Hum Gene Ther., 10(14):2273-2285 (1999); doi:10.1089/10430349950016924.
GenBank Database Accession No. AAH04107.1, Jul. 15, 2016, 2 pages.
Goodson, J. M., "Dental Applications" In Medical Applications of Controlled Release. vol. II. Applications and Evaluation. Robert S. Langer and Donald L. Wise (Eds.) Boca Raton, FL: CRC Press, 1984; pp. 115-138.
Grobet, L. et al., "A deletion in the bovine myostatin gene causes the double-muscled phenotype in cattle," Nat Genet., 17(1):71-74 (1997); doi:10.1038/ng0997-71.
Graham, F. L. & Van Der Eb, A. J., "A new technique for the assay of infectivity of human adenovirus 5 DNA," Virology, 52(2):456-467 (1983); doi:10.1016/0042-6822(73)90341-3.
Hackett, P. B. et al., "Evaluating risks of insertional mutagenesis by DNA transposons in gene therapy," Transl Res., 161(4):265-283 (2013); doi:10.1016/j.trsl.2012.12.005.
Hockemeyer, D. et al., "High efficient gene targeting of expressed and silent genes in human ESCs and iPSCs using zinc-finger nucleases," Nat Biotechnol., 27(9):851-857 (2009); doi: 10.1038/nbt.1562.
Hopwood, J. J. et al., "A fluorometric assay using 4-methylumbelliferyl alpha-L-iduronide for the estimation of alpha-L-iduronidase

(56) References Cited

OTHER PUBLICATIONS activity and the detection of Hurler and Scheie syndromes," Clin Chim Acta., 92(2):257-265 (1979).

Hudecek, M. et al., "Going non-viral: the Sleeping Beauty transposon system breaks on through to the clinical side," Crit Rev Biochem Mol Biol., 52(4):355-380 (2017).

Jasin, M., "Genetic manipulation of genomes with rare-cutting endonucleases," Trends Genet., 12(6):224-228 (1996); doi: 10.1016/0168-9525(96)10019-6.

Jinek, M. et al., "A programmable dual-RNA-guided DNA endonuclease in adaptive bacterial immunity," Science, 337(6096):816-821 (2012); doi: 10.1126/science.1225829.

Jinek, M. et al., "RNA-programmed genome editing in human cells," eLife, 2:e00471 (2013), 9 pages; doi: 10.7554/eLife.00471.

Khurana, T. S. & Davies, K. E., "Pharmacological strategies for muscular dystrophy," Nat Rev Drug Discov., 2(5):379-390 (2003); doi:10.1038/nrd1085.

Kim, Y.-G. et al., "Hybrid restriction enzymes: zinc finger fusions to Fok I cleavage domain," Proc Natl Acad Sci USA, 93(3):1156-1160 (1996); doi: 10.1073/pnas.93.3.1156.

Kierszenbaum, A. L., "Immune-Lymphatic System" in Histology and Cell Biology: An Introduction to Pathology. St. Louis: Mosby, 2002; Chapter 10, pp. 275.

Kindt, Thomas J., Goldsby, Richard A., and Osborne, Barbara A. (Eds.) "Overview of the Immune System." In Kuby Immunology, Sixth Edition. San Francisco: W.H. Freeman & Co.. 2007; p. 13. ISBN 1-4292-0211-4.

Koller, B. H. et al., "Germ-line transmission of a planned alteration made in a hypoxanthine phosphoribosyltransferase gene by homologous recombination in embryonic stem cells," Proc Natl Acad Sci USA., 86(22):8927-8931 (1989); doi: 10.1073/pnas.86.22.8927.

Kota, J. et al., "Follistatin gene delivery enhances muscle growth and strength in nonhuman primates," Sci Transl Med., 1(6):6ra15 (2009), 17 pages; doi:10.1126/scitranslmed.3000112.

Kung, S. K. P. et al. "A Murine Leukemia Virus (MuLV) Long Terminal Repeat Derived from Rhesus Macaques in the Context of a Lentivirus Vector and MuLV gag Sequence Results in High-Level Gene Expression in Human T Lymphocytes." J Virol., 74:3668-3681 (1999).

Langer, R. & Peppas, N., "Chemical and Physical Structure of Polymers as Carriers for Controlled Release of Bioactive Agents: A Review," J Macromol Sci Rev Macromol Chem., 23:61-126 (1983).

Lee, S-J. & Mcpherron, A. C., "Regulation of myostatin activity and muscle growth," Proc Natl Acad Sci USA, 98(16):9306-9311 (2001); doi:10.1073/pnas.151270098.

Li, Y. et al., "Mechanism of Neutralization by the Broadly Neutralizing HIV-1 Monoclonal Antibody VRC01," J Virol. 2011;85(17):8954-8967.

Lombardo, A. et al., "Gene editing in human stem cells using zinc finger nucleases and integrase-defective lentiviral vector delivery," Nat Biotechnol., 25(11):1298-306 (2007); doi: 10.1038/nbt1353.

Maclennan, I. C. M. & Hardie, D. L., "The Dynamic Structure of Antibody Responses" In Molecular Biology of B Cells. Honjo, T.; Alt, Frederick W.; and Neuberger, M. S. (Eds.), Amsterdam: Elsevier, 2004; pp. 187-201.

McIvor, R. S., "Drug-resistant dihydrofolate reductases: generation, expression and therapeutic application," Bone Marrow Transplantation, 18(Suppl. 3):S50-S54 (1996).

Mendell, J. R. et al., "A phase 1/2a follistatin gene therapy trial for becker muscular dystrophy," Mol Ther., 23(1):192-201(2015); doi:10.1038/mt.2014.200.

Miyahara, Y. et al., "A novel CAR-T therapy targeting MAGE-A4p230-239/HLA-A*02:01 complex for solid tumours". ESGCT XXV Anniversary Congress in Collaboration with the German Society for Gene Therapy, Oct. 17-20, 2017, Berlin, Germany. Human Gene Therapy, vol. 28, No. 12, Dec. 1, 2017, p. A36, Abstract P064.

Moehle, E. A. et al., "Targeted gene addition into a specified location in the human genome using designed zinc finger nucleases," Proc Natl Acad Sci USA, 104(9):3055-3060 (2007); doi: 10.1073/pnas.0611478104.

Murphy, K. et al., "Antibody-secreting plasma cells differentiate from activated B cells," In Janeway's Immunobiology. 7th Edition. New York: Garland Science, 2008; pp. 387-388.

Nakatani, M. et al., "Transgenic expression of a myostatin inhibitor derived from follistatin increases skeletal muscle mass and ameliorates dystrophic pathology in mdx mice," FASEB J., 22(2):477-487 (2008); doi:10.1096/fj.07-8673com.

Neron, S. et al., "Large-scale in vitro expansion of polyclonal human switched-memory B lymphocytes," PLoS One, 7(12):e51946 (2012), 8 pages; doi: 10.1371/journal.pone.0051946.

Paques, F. & Duchateau, P., "Meganucleases and DNA double-strand break-induced ecombination: perspectives for gene therapy," Curr Gene Ther., 7(1):49-66 (2007); doi: 10.2174/156652307779940216.

Paraskevas, F., "B Lymphocytes." In: Wintrobe's Clinical Hematology, 12th Edition, vol. 1. Hagerstown, MD: Lippincott Williams & Wilkins. 2009; p. 347.

Perler, F. B. et al., "Protein splicing elements: inteins and exteins—a definition of terms and recommended nomenclature," Nucleic Acids Res., 22(7):1125-1127 (1994); doi: 10.1093/nar/22.7.1125.

Rawstron, A. C. et al., "Immunophenotyping of plasma cells," Curr Protoc Cytom., May 2006; Chapter 6:Unit 6.23, 14 pages; doi:10.1002/0471142956.cy0623s36.

Rouet, P. et al., "Expression of a site-specific endonuclease stimulates homologous recombination in mammalian cells," Proc Natl Acad Sci USA., 91(13):6064-6068 (1994); doi: 10.1073/pnas.91.13.6064.

Schornack, S. et al., "Gene-for-gene-mediated recognition of nuclear-targeted AvrBs3-like bacterial effector proteins," J Plant Physiol., 163(3):256-272 (2006); doi:10.1016/j.jplph.2005.12.001.

Schuelke, M. et al., "Myostatin mutation associated with gross muscle hypertrophy in a child," N Engl J Med., 350(26):2682-2688 (2004); doi:10.1056/NEJMoa040933.

Segal, D. J., "Bacteria herald a new era of gene editing," eLife, 2:e00563 (2013), 3 pages; doi:10.7554/eLife.00563.

Shapiro-Shelef, M. & Calame, K., "Regulation of plasma-cell development," Nat Rev Immunol., 5(3):230-242 (2005); doi:10.1038/nri1572.

Shimasaki, S. et al., "Primary structure of the human follistatin precursor and its genomic organization," Proc Natl Acad Sci USA, 85(12):4218-4222 (1988).

Tey, S.-K. et al., "Inducible caspase 9 suicide gene to improve the safety of allodepleted T cells after haploidentical stem cell transplantation," Biol Blood Marrow Transplant., (8):913-924 (2007)I doi:10.1016/j.bbmt.2007.04.005.

Thomas, K. R. et al., "High frequency targeting of genes to specific sites in the mammalian genome," Cell, 44(3):419-428 (2007); doi: 10.1016/0092-8674(86)90463-0.

Urnov, F. D. et al., "Highly efficient endogenous human gene correction using designed zinc-finger nucleases," Nature, 435(7042):646-651 (2005); doi:10.1038/nature03556.

Wikipedia, The Free Encyclopedia., "Plasma cell." [online] https://en.wikipedia.org. Page Version ID: 404969441; Date of last revision: Dec. 30, 2010 09:54 UTC, originally retrieved Jan. 4, 2011, 4 pages.

Wu, X. et al., "Rational Design of Envelope Identifies Broadly Neutralizing Human Monoclonal Antibodies to HIV-1," Science, 329(5993):856-861 (2010); HHS Public Access Author Manuscript, 12 pages.

Zhao, C. et al., "Overcoming Insulin Insufficiency by Forced Follistatin Expression in β-cells of db/db Mice," Mol Ther., 23(5):866-874 (2015); doi:10.1038/mt.2015.29.

\* cited by examiner

Transduced on D0

Transduced on D4

Transduced on D5

Transduced on D6

METHODS FOR IN VITRO MEMORY B CELL DIFFERENTIATION AND TRANSDUCTION WITH VSV-G PSEUDOTYPED VIRAL VECTORS

CROSS REFERENCE TO RELATED APPLICATIONS

This application is a Continuation of U.S. application Ser. No. 14/776,283, filed on Sep. 14, 2015, now issued as U.S. Pat. No. 10,240,125, which is a U.S. national phase application of International Application No. PCT/US2014/027910, filed on Mar. 14, 2014, which claims priority to U.S. Provisional Application No. 61/785,490 filed on Mar. 14, 2013, each of which is incorporated by reference herein in its entirety.

BACKGROUND

Technical Field

The present disclosure relates to the in vitro differentiation of memory B cells to plasmablasts and plasma cells and genetic modification of these cells to express a protein of interest, such as a specific antibody or other protein therapeutic.

Description of the Related Art

After leaving the bone marrow, the B cell acts as an antigen presenting cell (APC) and internalizes antigens. Antigen is taken up by the B cell through receptor-mediated endocytosis and processed. Antigen is processed into antigenic peptides, loaded onto MHC II molecules, and presented on the B cell extracellular surface to CD4+ T helper cells. These T cells bind to the MHC II/antigen molecule and cause activation of the B cell. Upon stimulation by a T cell, the activated B cell begins to differentiate into more specialized cells. Germinal center B cells may differentiate into memory B cells or plasma cells. Most of these B cells will become plasmablasts, and eventually plasma cells, and begin producing large volumes of antibodies (see e.g., Trends Immunol. 2009 June; 30(6): 277-285; Nature Reviews, 2005, 5:231-242). The most immature blood cell that is considered a plasma cell instead of a B cell is the plasmablast. Plasmablasts secrete more antibodies than B cells, but less than plasma cells. They divide rapidly and are still capable of internalizing antigens and presenting them to T cells. A cell may stay in this state for several days, and then either die or irrevocably differentiate into a mature, fully differentiated plasma cell.

Terminally differentiated plasma cells express relatively few surface antigens, and do not express common pan-B cell markers, such as CD19 and CD20. Instead, plasma cells are identified through flow cytometry by their additional expression of CD38, CD78, the Interleukin-6 receptor and lack of expression of CD45. In humans, CD27 is a good marker for plasma cells, naive B cells are CD27−, memory B-cells are CD27+ and plasma cells are CD27++. CD38 and CD138 are expressed at high levels on plasma cells (See Wkipedia, The Free Encyclopedia., "Plasma cell" Page Version ID: 404969441; Date of last revision: 30 Dec. 2010 09:54 UTC, retrieved Jan. 4, 2011; See also: Jourdan et al. Blood. 2009 Dec 10; 114(25):5173-81; Trends Immunol. 2009 June; 30(6): 277-285; Nature Reviews, 2005, 5:231-242; Nature Med. 2010, 16:123-129; Neuberger, M. S.; Honjo, T.; Alt, Frederick W. (2004). Molecular biology of B cells. Amsterdam: Elsevier, pp. 189-191; Bertil Glader; Greer, John G.; John Foerster; Rodgers, George G.; Paraskevas, Frixos (2008). Wintrobe's Clinical Hematology, 2-Vol. Set. Hagerstwon, M D: Lippincott Williams & Wilkins. pp. 347; Walport, Mark; Murphy, Kenneth; Janeway, Charles; Travers, Paul J. (2008). Janeway's immunobiology. New York: Garland Science, pp. 387-388; Rawstron AC (May 2006). "Immunophenotyping of plasma cells". Curr Protoc Cytom).

Conventional pseudotype retroviruses have demonstrated insufficient infectivity of various tissues and cells. For example, a variety of stem cells including hematopoietic stem cell, and resting B and T cells can be important target cells in gene therapy or the like (Y. Hanazono, Molecular Medicine, Vol. 36, No. 7, 1999), but most of these cell types are found in a nondividing state (Abkowitz, J. L. et al., Nat Med, 2 (2), 190-7, 1996). In general, it is difficult to introduce genes using the retroviral vector exhibiting low infectivity against such nondividing cells.

Resting T and B cells can be efficiently transduced with retroviral vectors pseudotyped with measles virus, glycoproteins, H and F, on their surface (see e.g., Blood 2009 Oct. 8; 1 14(15):3173-80; Blood 2008 1 12:4843-4852). However, there are conflicting reports in the literature with regard to the ability of VSV-G pseudotyped viral vectors to transduce B cells (see e.g., Bovia et al., 2003 101:1727-1733; Serafini et al., Virology 325 (2004) 413-424).

Modifying nondividing cells is of particular importance for gene therapy and immunotherapy. However, the ability to differentiate and activate B cells in vitro is an important step in preparing modified B cells for infusion into subjects. Activated and dividing B cells are also not easily genetically modified. Thus, there remains a need in the art to improve the methods and reagents to efficiently genetically modify B cells in vitro. The present disclosure provides vectors and methods for modifying and differentiating/activating B cells such that they can be used effectively in prophylactic and therapeutic applications. The present disclosure provides this and other advantages as described in the detailed description.

SUMMARY OF THE INVENTION

One aspect of the present invention provides a method for expressing a nucleic acid of interest in a B cell comprising, contacting memory B cells with a composition comprising CD40L in combination with a B cell activating factor comprising one or more of the factors selected from the group consisting of IL-2, IL-10, IL-15, and p-ODN; contacting the B cells of (a) with a B cell activating factor comprising one or more of the factors selected from the group consisting of IL-2, IL-10, IL-6 and IL-15; under conditions such that the B cells in (b) express CD38; transducing the B cells in (b) with a retroviral vector pseudotyped with VSV-G, wherein said retroviral vector comprises the nucleic acid of interest operably linked to a promoter; and contacting the transduced B cells of (c) with a B cell activating factor comprising one or more of the factors selected from the group consisting of IFN-α; IFN-δ, IL-6 and IL-15; thereby expressing the nucleic acid of interest in the B cell. In one embodiment, the CD40L is sCD40L-his. In another embodiment, the transduction efficiency is about 20% and in some embodiments, the transduction efficiency is higher than 20%. In an additional embodiment, the retroviral vector is a lentiviral vector. In one embodiment, the nucleic acid of interest comprises a nucleic acid encoding at least an immunoglobulin VL and VH region. In yet another embodiment, the nucleic acid of interest encodes an antibody protein, or antigen-binding fragment thereof, a fusion protein or a DNA-encoded small molecule. In certain embodiments, the antibody is an anti-HIV antibody, an anti-RNA antibody, or an antibody that binds a protein involved in immune regulation. In another embodiment of the methods herein, the memory B cells are isolated from peripheral blood. In some embodiments of the methods, the B cells at step (b) of the methods are CD20−, CD38+ and CD138−. In yet another embodiment, the B cells of step (c) of the methods are CD20−, CD38+ and CD138+.

DETAILED DESCRIPTION

Figure 1:
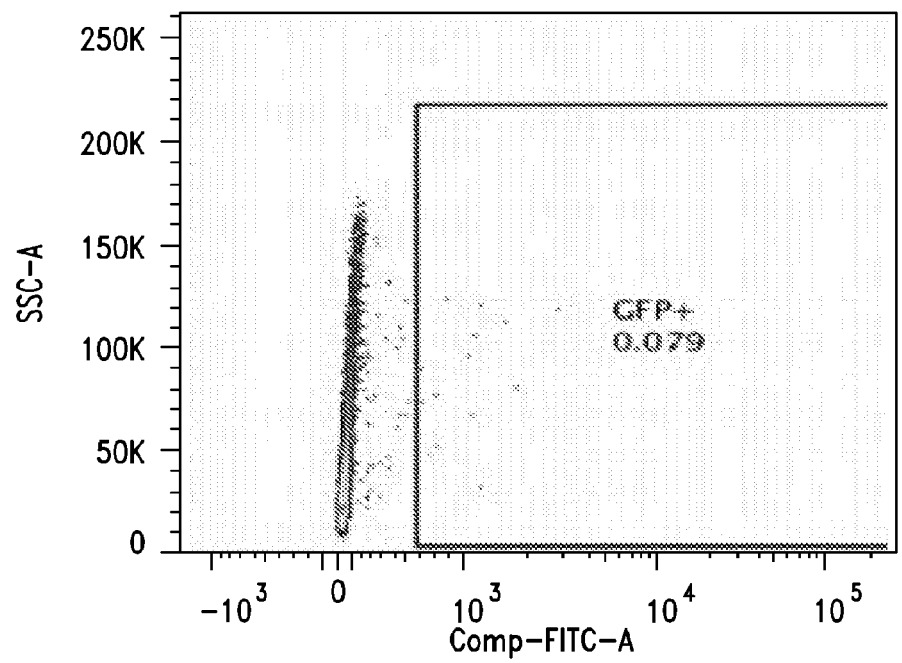
FIG. 1 is a series of flow cytometry dot plots that show transduction of B cells with green fluorescent protein (GFP) virus on Day 0 (D0), Day 4 (D4), Day 5 (D5), Day 6 (D6) and Day 7 (D7) of in vitro culture.
Figure 1:
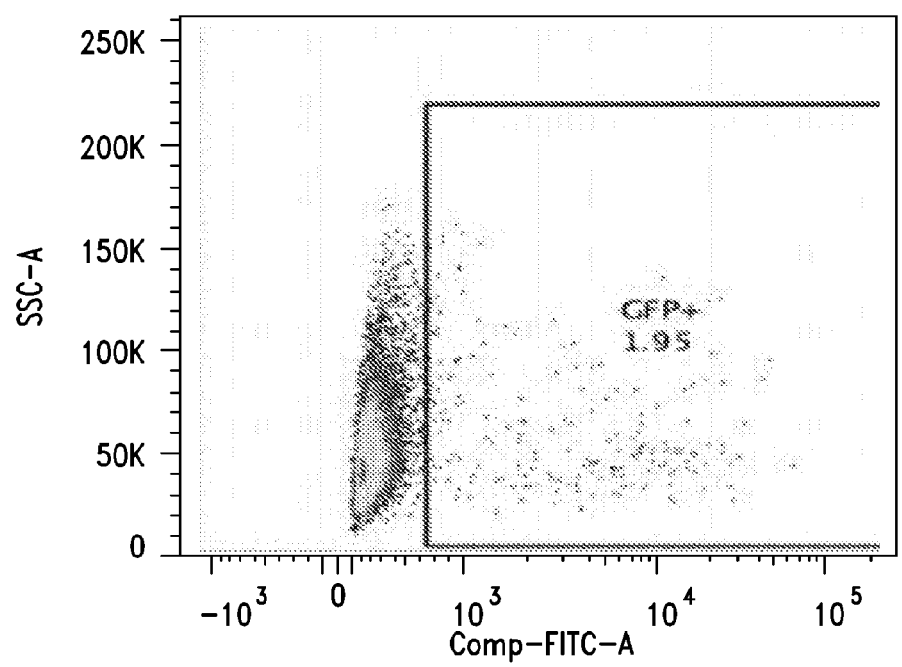
Figure 1:
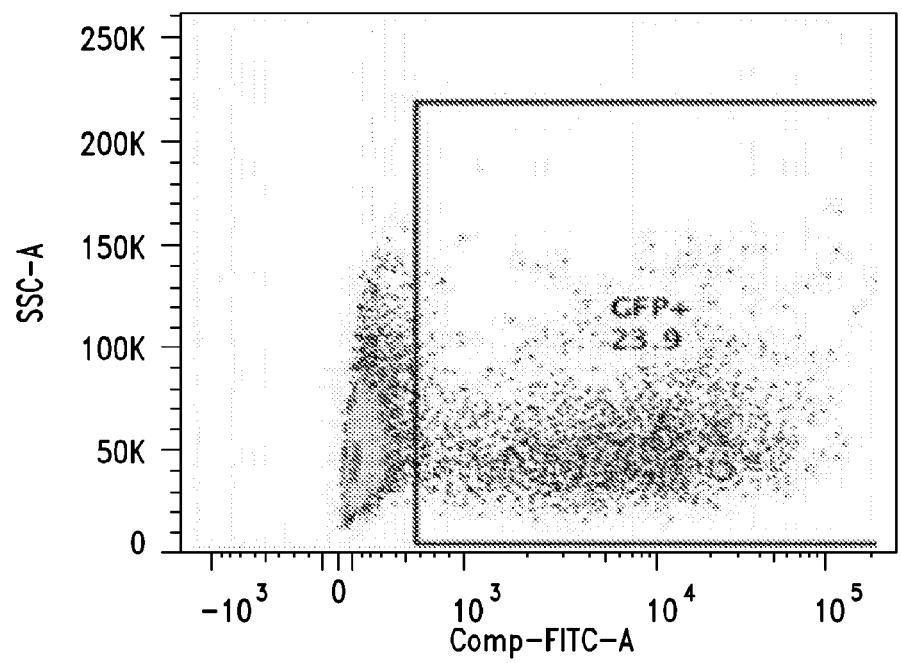
Figure 1:
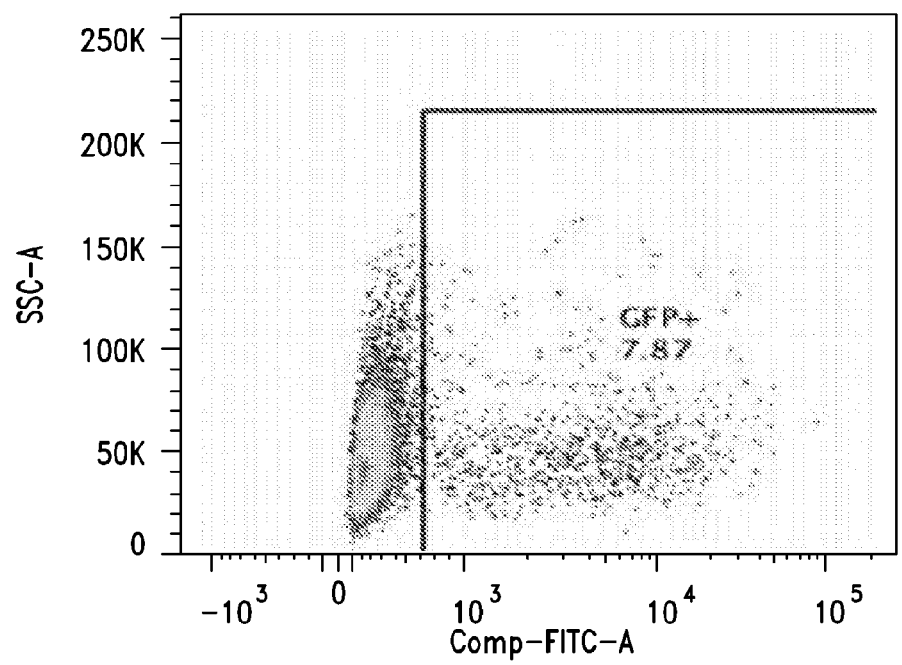
Figure 1:
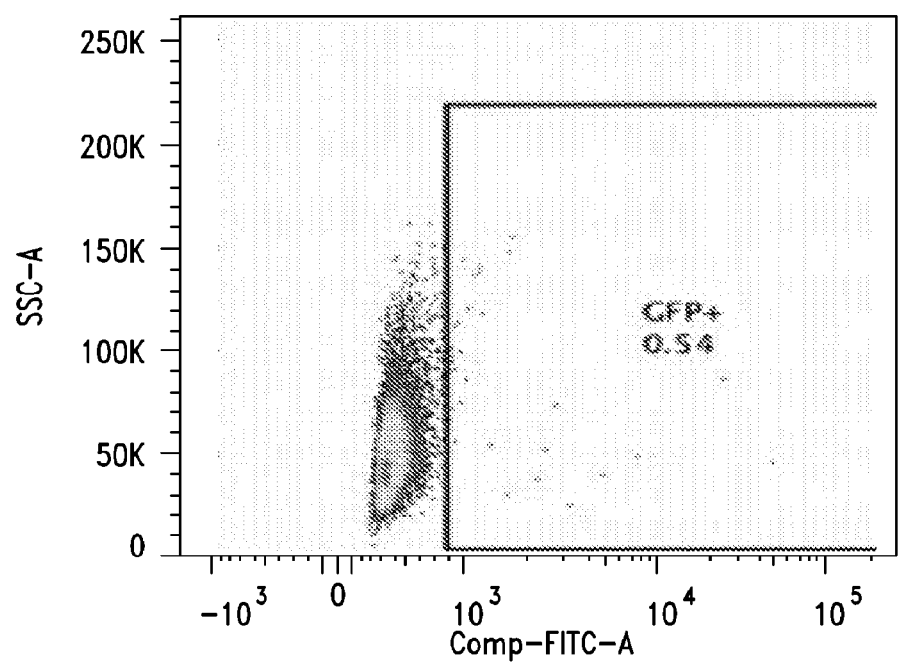

The present disclosure relates generally to culturing B cells in vitro under conditions so as to differentiate memory B cells into plasmablasts and plasma cells. The present invention further relates to genetically modifying B cells to express a gene of interest and activating and culturing the modified B cells so as to express the protein encoded by the gene of interest. These activated modified B cells are then administered to a subject. The compositions and methods described herein provide the ability to differentiate in vitro B cells derived from, for example, a simple blood draw, and then transduce the differentiated B cells with a nucleic acid of interest such that they secrete abundant amounts of the protein encoded by the nucleic acid of interest. One particular advantage of this system is that it only requires about 10 days to differentiate a resting memory B cell into a plasmablast or plasma cell, which can then be used for transduction and production of a protein of interest. Systems known in the art can take as long as 10 weeks. Thus, the present disclosure provides methods that require less time in culture providing commercial and safety advantages as compared to prior methods. An additional advantage of the present invention is that the in vitro culture methods provide increased transduction efficiency to about 20% transduction efficiency. This is an improvement over the low transduction efficiencies of methods known in the art. The present methods also do not require feeder cells which are burdensome for GMP grade production.

Methods of Culturing and Transducing B Cells

The prototypic example of cells for use with the transduction methods of the disclosure is B cells. In certain embodiments, the B cells to be used in the methods of this disclosure may be resting B cells, memory B cells, primed or activated B cells, myeloma cells, lymphocytic leukemia B cells, or B lymphoma cells. However, one of ordinary skill in the art will readily appreciate that the vectors and methods of the disclosure may be applied to other cell types. By way of example, cell types that may be cultured, differentiated, modified and activated include any typically nondividing or quiescent cell such as neuroblasts, hematopoietic stem cells and hematopoietic progenitor cells (CD34+ cells), mesenchymal stem cells, mesenchymal progenitor cells, neural and hepatic progenitor and stem cells, dendritic cells, T cells (CD8+ or CD4+ T cells), other leukocyte populations, pluripotent stem cells, multi-potent stem cells, etc. Accordingly, certain embodiments of the present disclosure provides populations of cells resulting from this methodology. In certain embodiments, the methods and vectors as described herein may be used to transduce any other cell type desired, such as hepatocytes, epithelial cells, osteoblasts, myocytes, fibroblasts, adipocytes etc.

"Quiescent", as used herein, refers to a cell state wherein the cell is not actively proliferating.

Prior to differentiation and transduction, a source of B cells is obtained from a subject. The term "subject" is intended to include living organisms in which an adaptive immune response can be elicited (e.g., mammals). Examples of subjects include humans, dogs, cats, mice, rats, and transgenic species thereof. B cells can be obtained from a number of sources, including peripheral blood mononuclear cells, bone marrow, lymph node tissue, cord blood, tissue from a site of infection, spleen tissue, and tumors. In certain embodiments of the present disclosure, any number of B cell lines available in the art, may be used. In certain embodiments of the methods described herein, B cells can be obtained from a unit of blood collected from a subject using any number of techniques known to the skilled artisan, such as FICOLL™ (copolymers of sucrose and epichlorohydrin that may be used to prepare high density solutions) separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the methods described herein, the cells are washed with phosphate buffered saline (PBS). In an alternative embodiment, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, PBS. Alternatively, the undesirable components of the apheresis sample may be removed and the cells directly resuspended in culture media.

B cells may be isolated from peripheral blood or leukapheresis using techniques known in the art. For example, PBMCs may be isolated using FICOLL™ (Sigma-Aldrich, St Louis, Mo.) and CD19+ B cells purified by negative or positive selection using any of a variety of antibodies known in the art, such as the Rosette tetrameric complex system (StemCell Technologies, Vancouver, Canada). In certain embodiments, memory B cells are isolated as described by Jourdan et al., (Blood. 2009 Dec. 10; 114(25):5173-81). For example, after removal of CD2+ cells using anti-CD2 magnetic beads, CD19+ CD27+ memory B cells can be sorted by FACS. Bone marrow plasma cells (BMPCs) can be purified using anti-CD138 magnetic microbeads sorting or other similar methods and reagents.

Other isolation kits are commercially available, such as R&D Systems' MagCellect Human B Cell Isolation Kit (Minneapolis, Minn.). In certain embodiments, resting B cells may be prepared by sedimentation on discontinuous Percoll gradients, as described in (Defranco et al., (1982) J. Exp. Med. 155:1523).

The present disclosure provides methods of culturing B cells, such as memory B cells, so as to promote differentiation and activation such that the B cells are efficiently transduced with viral vectors encoding a protein of interest and actively produce the transgene-encoded protein. In this regard, the B cells are activated and differentiate into plasma cells or plasmablasts or both. As would be recognized by the skilled person, plasma cells may be identified by cell surface protein expression patterns using standard flow cytometry methods. For example, terminally differentiated plasma cells express relatively few surface antigens, and do not express common pan-B cell markers, such as CD19 and CD20. Instead, plasma cells are identified through flow cytometry by their additional expression of CD38, CD78, CD138, the Interleukin-6 receptor and lack of expression of CD45. In humans, CD27 is a good marker for plasma cells, naive B cells are CD27−, memory B-cells are CD27+ and plasma cells are CD27++. CD38 and CD138 are expressed at high levels in plasma cells. Thus, in certain embodiments, the B cells used at the start of the in vitro culturing methods described herein are CD20+, CD38−, CD138− and they transduce poorly. However, in one embodiment, following certain steps of the culture methods described herein the cells are mostly CD20−, CD38+, CD138− and after further steps of the in vitro culture methods described herein, the cells are CD20−, CD38+, CD138+. Such cells can then be used for efficient transduction as described herein. In certain embodiments, it is desirable to differentiate and activate B cells prior to transduction. In one embodiment, the phenotype of the cells at day 6 may best be described as "activated" as they have cell surface phenotype of CD20− CD38− CD138− CD27+.

In one embodiment, the B cells may be contacted with a B cell activating factor, e.g., any of a variety of cytokines, growth factors or cell lines known to activate and/or differentiate B cells (see e.g., Fluckiger, et al. Blood 1998 92: 4509-4520; Luo, et al., Blood 2009 1 13: 1422-1431). Such factors may be selected from the group consisting of, but not limited to, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, and IL-35, IFN-γ, IFN-α, IFN-β, IFN-δ, C type chemokines XCL1 and XCL2, C-C type chemokines (to date including CCL1-CCL28) and CXC type chemokines (to date including CXCL1-CXCL17), and members of the TNF superfamily (e.g., TNF-α, 4-1 BB ligand, B cell activating factor (BLyS), FAS ligand, sCD40L (including multimeric versions of sCD40L; e.g., histidine-tagged soluble recombinant CD40L in combination with anti-polyhistidine mAb to group multiple sCD40L molecules together), Lymphotoxin, OX40L, RANKL, TRAIL), CpG, and other toll like receptor agonists (e.g., CpG). In one embodiment, In particular, B cells (including transduced B cells) may be contacted or cultured on feeder cells. In other embodiments, the culture system described herein is carried out in the absence of feeder cells, providing advantages over other systems known in the art that require feeder cells. Where feeder cells may be used, the feeder cells are a stromal cell line, e.g., the murine stromal cell lines S17 or MS5. In a further embodiment, purified CD19+ cells may be cultured in the presence of fibroblasts expressing CD40-ligand in the presence of B cell activating factor cytokines such as IL-10 and IL-4. CD40L may also be provided bound to a surface such as tissue culture plate or a bead. In another embodiment, purified B cells may be cultured in the presence or absence of feeder cells, with CD40L in presence of one or more cytokines or factors selected from IL-10, IL-4, IL-7, p-ODN, CpG DNA, IL-2, IL-15, IL6, IFN-α, and IFN-δ.

In another embodiment, B cell activating factors may be provided by transfection into the B cell or other feeder cell. In this context, one or more factors that promote differentiation of the B cell into an antibody secreting cell and/or one or more factors that promote the longevity of the antibody producing cell may be used. Such factors include, for example, Blimp-1, TRF4, anti-apoptotic factors like Bcl-xl or Bcl5, or constitutively active mutants of the CD40 receptor. Further, factors which promote the expression of downstream signaling molecules such as TNF receptor-associated factors (TRAFs) may also be used in the activation/differentiation of the B cells. In this regard, cell activation, cell survival, and antiapoptotic functions of the TNF receptor superfamily are mostly mediated by TRAF1-6 (see e.g., R. H. Arch, et al., Genes Dev. 12 (1998), pp. 2821-2830). Downstream effectors of TRAF signaling include transcription factors in the NF-κB and AP-1 family which can turn on genes involved in various aspects of cellular and immune functions. Further, the activation of NF-κB and AP-1 has been shown to provide cells protection from apoptosis via the transcription of antiapoptotic genes.

In an additional embodiment, Epstein Barr virus (EBV)-derived proteins may be useful for the activation/differentiation of B cells or to promote the longevity of the antibody producing cell. EBV-derived proteins include but are not limited to, EBNA-1, EBNA-2, EBNA-3, LMP-1, LMP-2, EBER, miRNAs, EBV-EA, EBV-MA, EBV-VCA and EBV-AN.

In certain embodiments, contact of the B cells with B cell activation factors using the methods provided herein leads to, among other things, cell proliferation, modulation of the IgM+ cell surface phenotype to one consistent with an activated mature B cell, secretion of Ig, and isotype switching. CD19+ B cells may be isolated using known and commercially available cell separation kits, such as the MiniMacs cell separation system (Miltenyi Biotech, Bergisch Gladbach, Germany). In certain embodiments, CD40L fibroblasts are irradiated before use in the methods described herein. In a further embodiment, progenitor cells or B cells may be cultured in the presence of one or more of IL-3, IL-7, Flt3 ligand, thrombopoietin, SCF, IL-2, IL-10, G-CSF and CpG. In certain embodiments, the methods include culturing the B cells or progenitors in the presence of one or more of the aforementioned factors in conjunction with transformed stromal cells (e.g., MS5) providing a low level of anchored CD40L, or CD40L bound to a plate or a bead.

Any of a variety of culture media may be used in the present methods as would be known to the skilled person (see e.g., Current Protocols in Cell Culture, 2000-2009 by John Wiley & Sons, Inc.). In one embodiment, media for use in the methods described herein includes, but is not limited to Is cove modified Dulbecco medium (with or without fetal bovine or other appropriate serum). Illustrative media also includes, but is not limited to, IMDM, RPMI 1640, AIM-V, DMEM, MEM, a-MEM, F-12, X-Vivo 15, and X-Vivo 20. In further embodiments, the medium may comprise a surfactant, an antibody, plasmanate or a reducing agent (e.g. N-acetyl-cysteine, 2-mercaptoethanol), or one or more antibiotics. In some embodiments, IL-6, soluble CD40L, and a cross-linking enhancer may also used. B cells or progenitor cells may be cultured under conditions and for sufficient time periods to achieve differentiation and activation desired. In certain embodiments, the B cells or progenitor cells are cultured under conditions and for sufficient time periods such that 10%, 15%, 20%, 25%, 30%, 35%, 40%, 45%, 50%, 55%, 60%, 65%, 70%, 75%, 80%, 85%, 90%, 95%, or even 100% of the B cells are differentiated and/or activated as desired. In one embodiment, the B cells are activated and differentiate into plasma cells. As would be recognized by the skilled person, plasmablasts and plasma cells may be identified by cell surface protein expression patterns using standard flow cytometry methods as described elsewhere herein, such as by expression of CD38, CD78, the Interleukin-6 receptor, $CD27^{high}$, CD138, and lack of expression of common pan-B cell markers, such as CD19 and CD20 and lack of expression of CD45. As would be understood by the skilled person, memory B cells are generally CD20+ CD19+ CD27+ CD38− while early plasmablasts are CD20− CD19+ CD27++ CD38++. In certain embodiments, the starting population in the methods described herein are CD20+, CD38−, CD138− (these cells generally transduce poorly). In one embodiment, the cells cultured using the methods described herein are CD20−, CD38+, CD138− and in another embodiment, the cells may have a phenotype of CD20−, CD38+, CD138+, depending on the day in culture that the cells are examined and which factors are used in the medium. In certain embodiments, cells are cultured for 1-7 days. In further embodiments, cells are cultured 7, 14, 21 days or longer. Thus, cells may be cultured under appropriate conditions for 1, 2, 3, 4, 5, 6, 7, 8, 9, 10, 11, 12, 13, 14, 15, 16, 17, 18, 19, 20, 21, 22, 23, 24, 25, 26, 27, 28, 29, or more days. Cells are replated, media and supplements may be added or changed as needed using techniques known in the art.

In certain embodiments, the B cells or progenitor cells (either before or after transduction) may be cultured under conditions and for sufficient time periods such that at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% of the cells are differentiated and activated to produce Ig and/or to express the transgene of interest.

The induction of B cell activation may be measured by techniques such as $^3$H-uridine incorporation into RNA (as B cells differentiate, RNA synthesis increases), or by $^3$H-thymidine incorporation, which measures DNA synthesis associated with cell proliferation. For optimal measurement of B cell proliferation, interleukin-4 (IL-4) may be added to the culture medium at an appropriate concentration, such as about 10 ng/ml.

Alternatively, B cell activation may be measured as a function of immunoglobulin secretion. For example, CD40L may be added to resting B cells together with IL-4 (e.g., 10 ng/ml) and IL-5 (e.g., 5 ng/ml) or other cytokines suited to activation of B cells. Flow cytometry may also be used for measuring cell surface markers typical of activated B cells. See e.g., Civin C I, Loken M R, Intl J. Cell Cloning ˆ 987; 5:1-16; Loken, M R, et al, Flow Cytometry Characterization of Erythroid, Lymphoid and Monomyeloid Lineages in Normal Human Bone Marrow, in Flow Cytometry in Hematology, Laerum O D, Bjerksnes R. eds., Academic Press, New York 1992; pp. 31-42; and LeBein T W, et al, Leukemia 1990; 4:354-358.

After culture for an appropriate period of time, such as from 2, 3, 4, 5, 6, 7, 8, 9, or more days, generally around 3 days, an additional volume of culture medium may be added. Supernatant from individual cultures may be harvested at various times during culture and quantitated for IgM and IgG1 as described in Noelle et al., (1991) J. Immunol. 146:1118-1124. In further embodiments, the cultures may be harvested and measured for expression of the transgene of interest using flow cytometry, ELISA, ELISPOT or other assay known in the art.

In further embodiments, enzyme-linked immunosorbent assay (ELISA) may be used for measuring IgM or other antibody isotype production or for production of the transgene of interest. In certain embodiments, IgG determinations may be made using commercially available antibodies such as goat antihuman IgG, as capture antibody, followed by detection using any of a variety of appropriate detection reagents such as biotinylated goat antihuman Ig, streptavidin alkaline phosphatase and substrate.

B cells, or other cells of interest, may be transduced with the retroviral vectors described herein using any of a variety of known techniques in the art (see, e.g., Science 12 Apr. 1996 272: 263-267; Blood 2007, 99:2342-2350; Blood 2009, 1 13:1422-1431; Blood 2009 Oct. 8; 1 14(15):3173-80; Blood. 2003; 101 (6):2167-2174; Current Protocols in Molecular Biology or Current Protocols in Immunology, John Wiley & Sons, New York, N.Y. (2009)). For example, PBMCs, B- or T-lymphocytes from donors and other B cell cancer cells such as B-CLLs may be isolated and cultured in IMDM medium or RPMI 1640 (GibcoBRL Invitrogen, Auckland, New Zealand) or other suitable medium as described herein, either serum-free or supplemented with 10% FCS and penicillin/streptomycin and/or other suitable supplements such as transferrin and/or insulin. In certain embodiments, cells are seeded at 1 E5 cells in 48-well plates and concentrated vector added at various doses that may be routinely optimized by the skilled person using routine methodologies. In certain embodiments, B cells may be transferred to MS5 cell monolayer in RPMI supplemented with 10% AB serum, 5% FCS, 50 ng/ml rhSCF, 10 ng/ml rhIL-15 and 5 ng/ml rhIL-2 and medium refreshed periodically as needed. As would be recognized by the skilled person, other suitable media and supplements may be used as desired.

In one embodiment, the B cells cultured as described herein to differentiate are contacted with a retroviral vector as described herein comprising a nucleic acid of interest operably linked to a promoter, under conditions sufficient to transduce at least a portion of the B cells. In one embodiment the B cells are contacted with a retroviral vector as described herein comprising a nucleic acid of interest operably linked to a promoter, under conditions sufficient to transduce at least 20% of the B cells. In a further embodiment, the B cells are contacted with a vector as described herein under conditions sufficient to transduce at least 15%, 20%, 25%, 30%, 35%, 40%, 45%, 50%, 55%, 60%, 70%, 75%, 80%, 85%, 90%, 95%, 96%, 97%, 98%, 99% or even 100% of the resting B cells. In one particular embodiment, the differentiated and activated B cells, cultured in vitro as described herein, are transduced, in which case the cultured differentiated/activated B cells are contacted with a vector as described herein under conditions sufficient to transduce at least 15%, 20%, 25%, 30%, 35%, 40%, 45%, 50%, 55%, 60%, 70%, 75%, 80%, 85%, 90%, 95%, 96%, 97%, 98%, 99% or even 100% of the differentiated and activated B cells.

In certain embodiments, prior to transduction the cells are prestimulated with *Staphylococcus Aureus* Cowan (SAC; Calbiochem, San Diego, Calif.); IL-2 for B cells or with anti-hCD3/anti-hCD28/IL-2 for T-cells, at appropriate concentrations known to the skilled person and routinely optimized. Other B cell activating factors (e.g., PMA), as are known to the skilled artisan and described herein may be used.

Viral Vectors

Certain embodiments employ viral vectors to transduce plasma cells such as B cells with the expression systems described herein. Examples of viral vectors include, without limitation, adenovirus-based vectors, adeno-associated virus (AAV)-based vectors, retroviral vectors, retroviral-adenoviral vectors, and vectors derived from herpes simplex viruses (HSVs), including amplicon vectors, replication-defective HSV and attenuated HSV (see, e.g., Krisky, Gene Ther. 5: 1517-30, 1998; Pfeifer, Annu. Rev. Genomics Hum. Genet. 2:177-21 1, 2001, each of which is incorporated by reference in its entirety).

Certain embodiments relate to the use of retroviral vectors, or vectors derived from retroviruses. "Retroviruses" are enveloped RNA viruses that are capable of infecting animal cells, and that utilize the enzyme reverse transcriptase in the early stages of infection to generate a DNA copy from their RNA genome, which is then typically integrated into the host genome. Examples of retroviral vectors Moloney murine leukemia virus (MLV)-derived vectors, retroviral vectors based on a Murine Stem Cell Virus, which provides long-term stable expression in target cells such as hematopoietic precursor cells and their differentiated progeny (see, e.g., Hawley et al., PNAS USA 93:10297-10302, 1996; Keller et al., Blood 92:877-887, 1998), hybrid vectors (see, e.g., Choi, et al., Stem Cells 19:236-246, 2001), and complex retrovirus-derived vectors, such as lentiviral vectors.

As noted above, certain embodiments employ lentiviral vectors. The term "lentivirus" refers to a genus of complex retroviruses that are capable of infecting both dividing and non-dividing cells. Examples of lentiviruses include HIV (human immunodeficiency virus; including HIV type 1, and HIV type 2), visna-maedi, the caprine arthritis-encephalitis virus, equine infectious anemia virus, feline immunodeficiency virus (FIV), bovine immune deficiency virus (BIV), and simian immunodeficiency virus (SIV). Lentiviral vectors can be derived from any one or more of these lentiviruses (see, e.g., Evans et al., Hum Gene Ther. 10:1479-1489, 1999; Case et al., PNAS USA 96:2988-2993, 1999; Uchida et al., PNAS USA 95:1 1939-1 1944, 1998; Miyoshi et al., Science 283:682-686, 1999; Sutton et al., J Virol 72:5781-5788, 1998; and Frecha et al., Blood. 1 12:4843-52, 2008, each of which is incorporated by reference in its entirety).

It has been documented that resting T and B cells can be transduced by a VSVG-coated LV carrying most of the HIV accessory proteins (vif, vpr, vpu, and nef) (see e.g., Frecha et al., 2010 Mol. Therapy 18:1748). In certain embodiments the retroviral vector comprises certain minimal sequences from a lentivirus genome, such as the HIV genome or the SIV genome. The genome of a lentivirus is typically organized into a 5' long terminal repeat (LTR) region, the gag gene, the pol gene, the env gene, the accessory genes (e.g., nef, vif, vpr, vpu, tat, rev) and a 3' LTR region. The viral LTR is divided into three regions referred to as U3, R (repeat) and U5. The U3 region contains the enhancer and promoter elements, the U5 region contains the polyadenylation signals, and the R region separates the U3 and U5 regions. The transcribed sequences of the R region appear at both the 5' and 3' ends of the viral RNA (see, e.g., "RNA Viruses: A Practical Approach" (Alan J. Cann, Ed., Oxford University Press, 2000); 0 Narayan, J. Gen. Virology. 70:1617-1639, 1989; Fields et al., Fundamental Virology Raven Press., 1990; Miyoshi et al., J Virol. 72:8150-7,1998; and U.S. Pat. No. 6,013,516, each of which is incorporated by reference in its entirety). Lentiviral vectors may comprise any one or more of these elements of the lentiviral genome, to regulate the activity of the vector as desired, or, they may contain deletions, insertions, substitutions, or mutations in one or more of these elements, such as to reduce the pathological effects of lentiviral replication, or to limit the lentiviral vector to a single round of infection.

Typically, a minimal retroviral vector comprises certain 5'LTR and 3'LTR sequences, one or more genes of interest (to be expressed in the target cell), one or more promoters, and a cis-acting sequence for packaging of the RNA. Other regulatory sequences can be included, as described herein and known in the art. The viral vector is typically cloned into a plasmid that may be transfected into a packaging cell line, such as a eukaryotic cell (e.g., 293-HEK), and also typically comprises sequences useful for replication of the plasmid in bacteria.

In certain embodiments, the viral vector comprises sequences from the 5' and/or the 3' LTRs of a retrovirus such as a lentivirus. The LTR sequences may be LTR sequences from any lentivirus from any species. For example, they may be LTR sequences from HIV, SIV, FIV or BIV. Preferably the LTR sequences are HIV LTR sequences.

In certain embodiments, the viral vector comprises the R and U5 sequences from the 5' LTR of a lentivirus and an inactivated or "self-inactivating" 3' LTR from a lentivirus. A "self-inactivating 3' LTR" is a 3' long terminal repeat (LTR) that contains a mutation, substitution or deletion that prevents the LTR sequences from driving expression of a downstream gene. A copy of the U3 region from the 3' LTR acts as a template for the generation of both LTR's in the integrated provirus. Thus, when the 3' LTR with an inactivating deletion or mutation integrates as the 5' LTR of the provirus, no transcription from the 5' LTR is possible. This eliminates competition between the viral enhancer/promoter and any internal enhancer/promoter. Self-inactivating 3' LTRs are described, for example, in Zufferey et al., J Virol. 72:9873-9880, 1998; Miyoshi et al., J Virol. 72:8150-8157, 1998; and Iwakuma et al., Wro/ogy 261: 120-132, 1999, each of which is incorporated by reference in its entirety. Self-inactivating 3' LTRs may be generated by any method known in the art. In certain embodiments, the U3 element of the 3' LTR contains a deletion of its enhancer sequence, preferably the TATA box, SpI and/or NF-kappa B sites. As a result of the self-inactivating 3' LTR, the provirus that is integrated into the host cell genome will comprise an inactivated 5' LTR.

The viral vectors provided herein typically comprises a gene that encodes a protein (or other molecule, such as siRNA) that is desirably expressed in one or more target cells. Preferably the gene of interest is located between the 5' LTR and 3' LTR sequences. Further, the gene of interest is preferably in a functional relationship with other genetic elements, for example, transcription regulatory sequences such as promoters and/or enhancers, to regulate expression of the gene of interest in a particular manner once the gene is incorporated into the target cell. In certain embodiments, the useful transcriptional regulatory sequences are those that are highly regulated with respect to activity, both temporally and spatially.

In certain embodiments, one or more additional genes may be incorporated as a safety measure, mainly to allow for the selective killing of infected target cells within a heterogeneous population, such as within a human patient. In one exemplary embodiment, the selected gene is a thymidine kinase gene (TK), the expression of which renders a target cell susceptible to the action of the drug gancyclovir. In a further embodiment, the suicide gene is a caspase 9 suicide gene.

In certain embodiments, a gene encoding a marker protein may be placed before or after the primary gene to allow for identification of cells that are expressing the desired protein. Certain embodiments incorporate a fluorescent marker protein, such as green fluorescent protein (GFP) or red fluorescent protein (RFP), along with the primary gene of interest. If one or more additional reporter genes are included, IRES sequences or 2A elements may also be included, separating the primary gene of interest from a reporter gene and/or any other gene of interest.

Certain embodiments may employ genes that encode one or more selectable markers. Examples include selectable markers that are effective in a eukaryotic cell or a prokaryotic cell, such as a gene for a drug resistance that encodes a factor necessary for the survival or growth of transformed host cells grown in a selective culture medium. Exemplary selection genes encode proteins that confer resistance to antibiotics or other toxins, e.g., G418, hygromycin B, puromycin, zeocin, ouabain, blasticidin, ampicillin, neomycin, methotrexate, or tetracycline, complement auxotrophic deficiencies, or supply may be present on a separate plasmid and introduced by co-transfection with the viral vector. Certain other embodiments may employ genes that encode one or cell surface receptors that can be used for tagging and detection or purification of transfected cells (e.g., low-affinity nerve growth factor receptor (LNGFR) or other such receptors useful as transduction tag systems. See e.g., Lauer et al., Cancer Gene Ther. 2000 March; 7(3):430-7).

Certain viral vectors such as retroviral vectors employ one or more heterologous promoters, enhancers, or both. In certain embodiments, the U3 sequence from a retroviral or lentiviral 5' LTR may be replaced with a promoter or enhancer sequence in the viral construct. Certain embodiments employ an "internal" promoter/enhancer that is located between the 5' LTR and 3' LTR sequences of the viral vector, and is operably linked to the gene of interest. A "functional relationship" and "operably linked" mean, without limitation, that the gene is in the correct location and orientation with respect to the promoter and/or enhancer, such that expression of the gene will be affected when the promoter and/or enhancer is contacted with the appropriate regulatory molecules. Any enhancer/promoter combination may be used that either regulates (e.g., increases, decreases) expression of the viral RNA genome in the packaging cell line, regulates expression of the selected gene of interest in an infected target cell, or both.

A promoter is an expression control element formed by a DNA sequence that permits binding of RNA polymerase and transcription to occur. Promoters are untranslated sequences that are located upstream (5') of the start codon of a selected gene of interest (typically within about 100 to 1000 bp) and control the transcription and translation of the coding polynucleotide sequence to which they are operably linked. Promoters may be inducible or constitutive. Inducible promoters initiate increased levels of transcription from DNA under their control in response to some change in culture conditions, such as a change in temperature.

A variety of promoters are known in the art, as are methods for operably linking the promoter to the polynucleotide coding sequence. Both native promoter sequences and many heterologous promoters may be used to direct expression of the selected gene of interest. Certain embodiments employ heterologous promoters, because they generally permit greater transcription and higher yields of the desired protein as compared to the native promoter.

Certain embodiments may employ heterologous viral promoters. Examples of such promoters include those obtained from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). Certain embodiments may employ heterologous mammalian promoter, such as the actin promoter, an immunoglobulin promoter, a heat-shock promoter, or a promoter that is associated with the native sequence of the gene of interest. Typically, the promoter is compatible with the target cell, such as a quiescent B-lymphocyte, an activated B-lymphocyte, a plasma B cell, a memory B cell or other lymphocyte target cell.

Certain embodiments may employ the one or more of the RNA polymerase II and III promoters. A suitable selection of RNA polymerase III promoters can be found, for example, in Paule and White. Nucleic Acids Research., Vol. 28, pp 1283-1298, 2000, which is incorporated by reference in its entirety. RNA polymerase II and III promoters also include any synthetic or engineered DNA fragments that can direct RNA polymerase II or III, respectively, to transcribe its downstream RNA coding sequences. Further, the RNA polymerase II or III (Pol II or III) promoter or promoters used as part of the viral vector can be inducible. Any suitable inducible Pol II or III promoter can be used with the methods described herein. Exemplary Pol II or III promoters include the tetracycline responsive promoters provided in Ohkawa and Taira, Human Gene Therapy, Vol. 11, pp 577-585, 2000; and Meissner et al., Nucleic Acids Research, Vol. 29, pp 1672-1682, 2001, each of which is incorporated by reference in its entirety.

Non-limiting examples of constitutive promoters that may be used include the promoter for ubiquitin, the CMV promoter (see, e.g., Karasuyama et al., J. Exp. Med. 169:13, 1989), the [beta]-actin (see, e.g., Gunning et al., PNAS USA 84:4831-4835, 1987), and the pgk promoter (see, e.g., Adra et al., Gene 60:65-74, 1987); Singer-Sam et al., Gene 32:409-417, 1984; and Dobson et al., Nucleic Acids Res. 10:2635-2637, 1982, each of which is incorporated by reference). Non-limiting examples of tissue specific promoters include the lck promoter (see, e.g., Garvin et al., Mol. Cell Biol. 8:3058-3064, 1988; and Takadera et al., Mol. Cell Biol. 9:2173-2180, 1989), the myogenin promoter (Yee et al., Genes and Development 7:1277-1289. 1993), and the thyl (see, e.g., Gundersen et al., Gene 1 13:207-214, 1992).

Additional examples of promoters include the ubiquitin-C promoter, the human [mu] heavy chain promoter or the Ig heavy chain promoter (e.g., MH), and the human [kappa] light chain promoter or the Ig light chain promoter (e.g., EEK), which are functional in B-lymphocytes. The MH promoter contains the human [mu] heavy chain promoter preceded by the [iota][Epsilon][mu] enhancer flanked by matrix association regions, and the EEK promoter contains the [kappa] light chain promoter preceded an intronic enhancer ([iota][Epsilon][kappa]), a matrix associated region, and a 3' enhancer (3[Epsilon][kappa]) (see, e.g., Luo et al., Blood. 1 13:1422-1431, 2009, and published U.S. patent application 20100203630). Accordingly, certain embodiments may employ one or more of these promoter or enhancer elements.

As noted above, certain embodiments may employ enhancer elements, such as an internal enhancer, to increase expression of the gene of interest. Enhancers are cis-acting elements of DNA, usually about 10 to 300 bp in length, that act on a promoter to increase its transcription. Certain enhancer sequences may be derived from mammalian genes (e.g., globin, elastase, albumin, α-fetoprotein, insulin), such as the [iota][Epsilon][mu] enhancer, the [iota][Epsilon][kappa] intronic enhancer, and the 3' [Epsilon][kappa] enhancer. Also included are enhancers from a eukaryotic virus, including the SV40 enhancer on the late side of the replication origin (bp 100-270), the cytomegalovirus early promoter enhancer, the polyoma enhancer on the late side of the replication origin, and adenovirus enhancers. Enhancers may be spliced into the vector at a position 5' or 3' to the antigen-specific polynucleotide sequence, but are preferably located at a site 5' from the promoter. Persons of skill in the art will select the appropriate enhancer based on the desired expression pattern.

In certain embodiments, promoters may be selected to allow for inducible expression of the gene. A number of systems for inducible expression are known in the art, including the tetracycline responsive system and the lac operator-repressor system. It is also contemplated that a combination of promoters may be used to obtain the desired expression of the gene of interest. The skilled artisan will be able to select a promoter based on the desired expression pattern of the gene in the organism and/or target cell of interest.

Certain viral vectors contain cis-acting packaging sequences to promote incorporation of the genomic viral RNA into the viral particle. Examples include psi-sequences. Such cis-acting sequences are known in the art. In certain embodiments, the viral vectors described herein may express two or more genes, which may be accomplished, for example, by incorporating an internal promoter that is operably linked to each separate gene beyond the first gene, by incorporating an element that facilitates co-expression such as an internal ribosomal entry sequence (IRES) element (U.S. Pat. No. 4,937,190, incorporated by reference) or a 2A element, or both. Merely by way of illustration, IRES or 2A elements may be used when a single vector comprises sequences encoding each chain of an immunoglobulin molecule with a desired specificity. For instance, the first coding region (encoding either the heavy or light chain) may be located immediately downstream from the promoter, and the second coding region (encoding the other chain) may be located downstream from the first coding region, with an IRES or 2A element located between the first and second coding regions, preferably immediately preceding the second coding region. In other embodiments, an IRES or 2A element is used to co-express an unrelated gene, such as a reporter gene, a selectable marker, or a gene that enhances immune function. Examples of IRES sequences that can be used include, without limitation, the IRES elements of encephalomyelitis virus (EMCV), foot-and-mouth disease virus (FMDV), Theiler's murine encephalomyelitis virus (TMEV), human rhinovirus (HRV), coxsackievirus (CSV), poliovirus (POLIO), Hepatitis A virus (HAV), Hepatitis C virus (HCV), and Pestiviruses (e.g., hog cholera virus (HOCV) and bovine viral diarrhea virus (BVDV)) (see, e.g., Le et al., Virus Genes 12:135-147, 1996; and Le et al., Nuc. Acids Res. 25:362-369, 1997, each of which is incorporated by reference in their entirety). One example of a 2A element includes the F2A sequence from foot-and-mouth disease virus.

In certain embodiments, the viral vectors provided herein may also contain additional genetic elements to achieve a desired result. For example, certain viral vectors may include a signal that facilitates nuclear entry of the viral genome in the target cell, such as an HIV-1 flap signal. As a further example, certain viral vectors may include elements that facilitate the characterization of the provirus integration site in the target cell, such as a tRNA amber suppressor sequence. Certain viral vectors may contain one or more genetic elements designed to enhance expression of the gene of interest. For example, a woodchuck hepatitis virus responsive element (WRE) may be placed into the construct (see, e.g., Zufferey et al., J. Virol. 74:3668-3681, 1999; and Deglon et al., Hum. Gene Ther. 11:179-190, 2000, each of which is incorporated by reference in its entirety). As another example, a chicken [beta]-globin insulator may also be included in the viral construct. This element has been shown to reduce the chance of silencing the integrated provirus in the target cell due to methylation and heterochromatinization effects. In addition, the insulator may shield the internal enhancer, promoter and exogenous gene from positive or negative positional effects from surrounding DNA at the integration site on the chromosome. Certain embodiments employ each of these genetic elements. In another embodiment, the viral vectors provided herein may also contain a Ubiquitous Chromatin Opening Element (UCOE) to increase expression (see e.g., Zhang F, et al., Molecular Therapy: The journal of the American Society of Gene Therapy 2010 September; 18(9):1640-9.)

In certain embodiments, the viral vectors (e.g., retroviral, lentiviral) provided herein are "pseudo-typed" with one or more selected viral glycoproteins or envelope proteins, mainly to target selected cell types. Pseudo-typing refers to generally to the incorporation of one or more heterologous viral glycoproteins onto the cell-surface virus particle, often allowing the virus particle to infect a selected cell that differs from its normal target cells. A "heterologous" element is derived from a virus other than the virus from which the RNA genome of the viral vector is derived. Typically, the glycoprotein-coding regions of the viral vector have been genetically altered such as by deletion to prevent expression of its own glycoprotein. Merely by way of illustration, the envelope glycoproteins gp41 and/or gp120 from an HIV-derived lentiviral vector are typically deleted prior to pseudo-typing with a heterologous viral glycoprotein.

In certain embodiments, the viral vector is pseudo-typed with a heterologous viral glycoprotein that targets B lymphocytes. In certain embodiments, the viral glycoprotein allows selective infection or transduction of resting or quiescent B lymphocytes. In certain embodiments, the viral glycoprotein allows selective infection of B lymphocyte plasma cells, plasmablasts, and activated B cells. In certain embodiments, the viral glycoprotein allows infection or transduction of quiescent B lymphocytes, plasmablasts, plasma cells, and activated B cells. In certain embodiments, viral glycoprotein allows infection of B cell chronic lymphocyte leukemia cells. In one embodiment, the viral vector is pseudo-typed with VSV-G. In another embodiment, the heterologous viral glycoprotein is derived from the glycoprotein of the measles virus, such as the Edmonton measles virus. Certain embodiments pseudo-type the measles virus glycoproteins hemagglutinin (H), fusion protein (F), or both (see, e.g., Frecha et al., Blood. 1 12:4843-52, 2008; and Frecha et al., Blood. 1 14:3173-80, 2009, each of which is incorporated by reference in its entirety). In one embodiment, the viral vector is pseudo-typed with gibbon ape leukemia virus (GALV). In further embodiments, the viral vector comprises an embedded antibody binding domain, such as one or more variable regions (e.g., heavy and light chain variable regions) which serves to target the vector to a particular cell type.

Generation of viral vectors can be accomplished using any suitable genetic engineering techniques known in the art, including, without limitation, the standard techniques of restriction endonuclease digestion, ligation, transformation, plasmid purification, PCR amplification, and DNA sequencing, for example as described in Sambrook et al. (Molecular Cloning: A Laboratory Manual. Cold Spring Harbor Laboratory Press, N.Y. (1989)), Coffin et al. (Retroviruses. Cold Spring Harbor Laboratory Press, N.Y. (1997)) and "RNA Viruses: A Practical Approach" (Alan J. Cann, Ed., Oxford University Press, (2000)).

Any variety of methods known in the art may be used to produce suitable retroviral particles whose genome comprises an RNA copy of the viral vector. As one method, the viral vector may be introduced into a packaging cell line that packages the viral genomic RNA based on the viral vector into viral particles with a desired target cell specificity. The packaging cell line typically provides in trans the viral proteins that are required for packaging the viral genomic RNA into viral particles and infecting the target cell, including the structural gag proteins, the enzymatic pol proteins, and the envelope glycoproteins.

In certain embodiments, the packaging cell line may stably express certain of the necessary or desired viral proteins (e.g., gag, pol) (see, e.g., U.S. Pat. No. 6,218,181, herein incorporated by reference). In certain embodiments, the packaging cell line may be transiently transfected with plasmids that encode certain of the necessary or desired viral proteins (e.g., gag, pol, glycoprotein), including the measles virus glycoprotein sequences described herein. In one exemplary embodiment, the packaging cell line stably expresses the gag and pol sequences, and the cell line is then transfected with a plasmid encoding the viral vector and a plasmid encoding the glycoprotein. Following introduction of the desired plasmids, viral particles are collected and processed accordingly, such as by ultracentrifugation to achieve a concentrated stock of viral particles. Exemplary packaging cell lines include 293 (ATCC CCL X), HeLa (ATCC CCL 2), D17 (ATCC CCL 183), MDCK (ATCC CCL 34), BHK (ATCC CCL-10) and Cf2Th (ATCC CRL 1430) cell lines.

Gene/Nucleic Acid of Interest

As used herein "gene of interest" or "gene" or "nucleic acid of interest" refers to a nucleic acid of interest encoding a protein of interest to be expressed in the target transduced cell. While the term "gene" may be used, this is not to imply that this is a gene as found in genomic DNA and is used interchangeably with the term "nucleic acid". Generally, the nucleic acid of interest provides suitable nucleic acid for encoding the protein of interest and may comprise cDNA or DNA and may or may not include introns but generally does not include introns. As noted elsewhere, the nucleic acid of interest is operably linked to expression control sequences to effectively express the protein of interest in the target cell. In certain embodiments, the vectors described herein may comprise two or more genes of interest, and may include 2, 3, or 4 genes of interest, such as for example, the heavy and light chains of an immunoglobulin that may be organized using an internal promoter as described herein.

The recitation "polynucleotide" or "nucleic acid" as used herein designates mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA and RNA. The nucleic acid or gene of interest may be any nucleic acid encoding a protein of interest. A protein of interest for use as described herein comprises any protein providing an activity desired. In this regard, a protein of interest includes, but is not limited to, an antibody or antigen-binding fragment thereof, a cell surface receptor, a secreted protein such as a cytokine (lymphokines, interleukins, interferons, or chemokines), a DNA-encoded small molecule (see e.g., Nature Chemical Biology 5, 647-654 (2009)), or an adhesion molecule. In one embodiment, the nucleic acid encodes an antibody or antigen-binding fragment thereof. Exemplary antigen binding fragments include domain antibodies, sFv, scFv, Fab, Fab', F(ab')2, Fv). In one embodiment, the antibody encoded by the nucleic acid comprises at least the antigen binding domain of the HIV neutralizing antibody, b12 (see, e.g., J Virol 2003, 77:5863-5876; J Virol. 1994 August; 68(8):4821-8; Proc Natl Acad Sci USA. 1992, 89:9339-9343; exemplary sequences are provided in GenBank Accession Nos. for the b12 light chain (AAB26306.1 GI 299737) and heavy chain (AAB26315.1 GI 299746)). In a further embodiment, the antibody encoded by the nucleic acid of interest comprises Fuzeon™ (T-20/enfuvirtide/pentafuside/DP-178). DP-178 is an amino acid sequence from gp41 on HIV and interferes with HIV's ability to fuse with its target cell. Fuzeon may be produced synthetically using methods known to the skilled person (see e.g., 2001 J. Virol. 75:3038-3042; It should be noted that it is highly unlikely that the methods described in this paper resulted in secretion of a therapeutic dose of the DP-178 peptide).

In one particular embodiment, the nucleic acid of interest encodes an immunologically active protein. In certain embodiments, a nucleic acid of interest encodes a protein, or a biologically active fragment thereof, that induces an immune vaccine-like reaction through the presentation of the protein on the surface of a B cell, T cell or other immune cell. In certain embodiments, the protein of interest influences the regulation of B cells, for example but not limited to promoting cell division, promoting differentiation into different B lineages, inactivating or killing cells, or regulates production or activity of other introduced DNA elements. Interleukins are known to the skilled person and to date include IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, secreted form of the p28 subunit of IL27, IL-28, IL-29, IL-30, IL-31, IL-32, IL-33, IL-34, and IL-35. Interferons include IFN-[gamma], IFN-α, IFN-[beta] and IFN-[omega]. The chemokines contemplated for use herein include the C type chemokines XCL1 and XCL2, C-C type chemokines (to date including CCL1-CCL28) and CXC type chemokines (to date including CXCL1-CXCL17). Also contemplated as a gene of interest are members of the TNF superfamily (e.g., TNF-a, 4-1 BB ligand, B cell activating factor, FAS ligand, Lymphotoxin, OX40L RANKL, and TRAIL).

In certain embodiments, the protein of interest induces immunological tolerance. In this regard, the protein of interest may comprise an IgG-antigen fusion protein (see e.g., Cellular Immunology 235(1), 2005, 12-20).

In a further embodiment, the gene(s) of interest encodes one or more factors that promote differentiation of the B cell into an antibody secreting cell and/or one or more factors that promote the longevity of the antibody producing cell. Such factors include, for example, Blimp-1, TRF4, antiapoptotic factors like Bcl-xl or Bcl5, constitutively active mutants of the CD40 receptor. Further genes of interest encode factors which promote the expression of downstream signaling molecules such as TNF receptor-associated factors (TRAFs). In this regard, cell activation, cell survival, and antiapoptotic functions of the TNF receptor superfamily are mostly mediated by TRAF 1-6 (see e.g., R. H. Arch, et al., Genes Dev. 12 (1998), pp. 2821-2830). Downstream effectors of TRAF signaling include transcription factors in the NF-κB and AP-1 family which can turn on genes involved in various aspects of cellular and immune functions. Further, the activation of NF-[kappa][Beta] and AP-1 has been shown to provide cells protection from apoptosis via the transcription of anti-apoptotic genes.

In an additional embodiment, the nucleic acid(s) of interest encodes one or more Epstein Barr virus (EBV)-derived proteins. EBV-derived proteins include but are not limited to, EBNA-1, EBNA-2, EBNA-3, LMP-1, LMP-2, EBER, EBV-EA, EBV-MA, EBV-VCA and EBV-AN. In one particular embodiment, the nucleic acid of interest encodes an antibody or an antigen-binding fragment thereof. In this regard, the antibody may be a natural antibody or a custom, recombinantly engineered antibody. Fusion proteins comprising an antibody or portion thereof are specifically contemplated to be encoded by the vectors described herein.

In one embodiment, an antibody or fragment thereof according to the present disclosure has an amino acid sequence of an anti-HIV antibody, such as the m36 anti-HIV antibody (see e.g., Proc Natl Acad Sci USA. 2008 Nov. 4; 105(44):17121-6), or an amino acid molecule having at least 60%, 80%, 85%, 90%, 95%, 96%, 97%, 98% or 99% sequence identity with an amino acid sequence of an anti-HIV antibody, such as m36. In particular, fusion proteins comprising m36, or derivatives thereof, are specifically contemplated, such as m36L2CD4Fc (see e.g., Antiviral Research volume 88, Issue 1, October 2010, Pages 107-1 15).

In a further embodiment, the antibody encoded by the transgene of the disclosure binds to an autoantigen. In certain embodiments, the autoantigen in this regard is associated with the development of multiple sclerosis or Type 1 diabetes, including but not limited to MBP, alphaB-crystallin, S100beta, proteolipid protein (PLP), HSP105, epithelial isoform of bullous pemphigoid (BP) antigen 1 (BPAG1-e), lipids, and myelin oligodendrocyte glycoprotein (MOG)-alpha and MOG-beta isoforms or any of a variety of islet cell autoantigens (e.g., sialoglycolipid, glutamate decarboxylase, insulin, insulin receptor, 38 kD, bovine serum albumin, glucose transporter, hsp 65, carboxypeptidase H, 52 kD, ICA 12/ICA512, 150 kD, and RIN polar). Antibodies to these autoantigens are known in the art and may be sequenced and made recombinantly using routine techniques (see e.g., J. Clin. Invest. 107(5): 555-564 (2001)).

In a further embodiment, the antibody binds to a cancer-associated antigen. Cancer-associated antigens may be derived from a variety of tumor proteins. Illustrative tumor proteins useful in the present disclosure include, but are not limited to any one or more of, p53, MAGE-A1, MAGE-A2, MAGE-A3, MAGE-A4, MAGE-A6, MAGE-A10, MAGE-A12, BALE, DAM-6, -10, GAGE-1, -2, -8, GAGE-3, -4, -5, -6, -7B, NA88-A, NY-ESO-1, MART-1, MC1 R, Gp100, PSA, PSM, Tyrosinase, TRP-1, TRP-2, ART-4, CAMEL, CEA, Cyp-B, Her2/neu (e.g., the antibody may be derived from the Her2-specific mAb, Herceptin®), hTERT, hTRT, iCE, MUC1, MUC2, PRAME, P15, RU1, RU2, SART-1, SART-3, WT1, AFP, [beta]-catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, ETV6/AML, LDLR/FUT, Pml/RARa, and TEL/AML1. These and other tumor proteins are known to the skilled artisan.

In further embodiments, the nucleic acid of interest encodes a peptide or other binding domain with a particular functional attribute, such as, but not limited to, an inhibitory activity, ability to induce cell death in cancer cells, or ability to slow or inhibit cancer cell proliferation. In this regard, in one embodiment, a peptide or binding domain encoded by the nucleic acid of interest may bind any of the target proteins described herein, such as a cancer-associated antigen as described above, CD4, HIV gp120 or other viral protein, ICAM-3, DC-SIGN (see e.g., U.S. Pat. No. 7,301, 010). In certain embodiments, the peptides may be derived from pathogenic and nonpathogenic bacteria and green plants. Illustrative peptides are disclosed in U.S. Pat. Nos. 7,084,105, 7,301,010, 7,338,766, 7,381,701, 7,491,394, 7,511,117, 7,556,810. In one embodiment, the nucleic acid of interest encodes azurin-p28 (NSC745104) a peptide inhibitor of p53 ubiquitination (see e.g., Cancer Chemother Pharmacol 2010, DOI 10.1007/S00280-010-1518-3; U.S. Pat. No. 7,084,105). In a further embodiment, the nucleic acid of interest encodes a factor known as Ghrelin, which induces appetite and can be used to treat cancer patients (see e.g., Obes Facts. 2010 3:285-92; FASEB J. 18 (3): 439-56). In another embodiment, the nucleic acid of interest encodes a binding peptide that binds to and inhibits angiopoietin 1 and 2 (see, e.g., AMG386, an Fc fragment of an antibody (peptibody) used to treat cancer; In certain embodiments, tumor antigens may be identified directly from an individual with cancer. In this regard, screens can be carried out using a variety of known technologies. For example, in one embodiment, a tumor biopsy is taken from a patient, RNA is isolated from the tumor cells and screened using a gene chip (for example, from Affymetrix, Santa Clara, Calif.) and a tumor antigen is identified. Once the tumor target antigen is identified, it may then be cloned, expressed and purified using techniques known in the art.

In one embodiment, the nucleic acid of interest encodes iduronidase (IDUA) for treatment or prevention of mucopolysaccharidosis type I (MPS I or Hurler syndrome). In another embodiment, the nucleic acid of interest encodes factor VII for treatment or prevention of hemophilia. In one embodiment, the nucleic acid of interest encodes lecithin-cholesterol acyltransferase (LCAT) useful for treatment or prevention of, e.g., LCAT deficiency and atherosclerosis. In another embodiment, the nucleic acid of interest encodes Apolipoprotein A-1 Milano (ApoA-1 Milano) for treatment or prevention of cardiovascular diseases and disorders, such as, e.g., atherosclerosis. In one embodiment, the nucleic acid of interest encodes lipoprotein lipase (LPL) for treatment or prevention of LPL deficiency. In another embodiment, the nucleic acid of interest encodes a broadly neutralizing antibody (bNAb), or a fusion protein thereof, that binds to and neutralizes multiple HIV-1 strains (e.g., b12). In yet another embodiment, the nucleic acid of interest encodes phenylalanine hydroxylase for treatment or prevention of phenykentonuria (PKU).

An "antibody", as used herein, includes both polyclonal and monoclonal antibodies; primatized (e.g., humanized); murine; mouse-human; mouse-primate; and chimeric; and may be an intact molecule, a fragment thereof (such as scFv, Fv, Fd, Fab, Fab' and F(ab)'2 fragments), or multimers or aggregates of intact molecules and/or fragments; and may occur in nature or be produced, e.g., by immunization, synthesis or genetic engineering; an "antibody fragment," as used herein, refers to fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'2, scFv, light chain variable region (VL), heavy chain variable region (VH), and combinations thereof. Sources include antibody gene sequences from various species (which can be formatted as antibodies, sFvs, scFvs or Fabs, such as in a phage library), including human, camelid (from camels, dromedaries, or llamas; Hamers-Casterman et al. (1993) Nature, 363:446 and Nguyen et al. (1998) J. Mol. Biol., 275:413), shark (Roux et al. (1998) Proc. Nat'l. Acad. Sci. (USA) 95:1 1804), fish (Nguyen et al. (2002) Immunogenetics, 54:39), rodent, avian, ovine, sequences that encode random peptide libraries or sequences that encode an engineered diversity of amino acids in loop regions of alternative non-antibody scaffolds, such as fibrinogen domains (see, e.g., Weisel et al. (1985) Science 230:1388), Kunitz domains (see, e.g., U.S. Pat. No. 6,423,498), lipocalin domains (see, e.g., WO 2006/095164), V-like domains (see, e.g., US Patent Application Publication No. 2007/0065431), C-type lectin domains (Zelensky and Gready (2005) FEBS J. 272:6179), mAb<2> or Fcab™ (see, e.g., PCT Patent Application Publication Nos. WO 2007/098934; WO 2006/072620), or the like.

Terms understood by those in the art as referring to antibody technology are each given the meaning acquired in the art, unless expressly defined herein. For example, the terms "VL" and "VH" refer to the variable binding region derived from an antibody light and heavy chain, respectively. The variable binding regions are made up of discrete, well-defined sub-regions known as "complementarity determining regions" (CDRs) and "framework regions" (FRs). The terms "O." and "CH" refer to an "immunoglobulin constant region," i.e., a constant region derived from an antibody light or heavy chain, respectively, with the latter region understood to be further divisible into Cm, CH2, CH3 and CH4 constant region domains, depending on the antibody isotype (IgA, IgD, IgE, IgG, IgM) from which the region was derived. A portion of the constant region domains makes up the Fc region (the "fragment crystallizable" region), which contains domains responsible for the effector functions of an immunoglobulin, such as ADCC (antibody-dependent cell-mediated cytotoxicity), CDC (complement-dependent cytotoxicity) and complement fixation, binding to Fc receptors, greater half-life in vivo relative to a polypeptide lacking an Fc region, protein A binding, and perhaps even placental transfer (see Capon et al. (1989) Nature, 337:525). Further, a polypeptide containing an Fc region allows for dimerization or multimerization of the polypeptide.

The domain structure of immunoglobulins is amenable to engineering, in that the antigen binding domains and the domains conferring effector functions may be exchanged between immunoglobulin classes and subclasses. Immunoglobulin structure and function are reviewed, for example, in Harlow et al., Eds., Antibodies: A Laboratory Manual, Chapter 14 (Cold Spring Harbor Laboratory, Cold Spring Harbor, 1988). An extensive introduction as well as detailed information about all aspects of recombinant antibody technology can be found in the textbook Recombinant Antibodies (John Wiley & Sons, NY, 1999). A comprehensive collection of detailed antibody engineering lab Protocols can be found in R. Kontermann and S. Dubel, Eds., The Antibody Engineering Lab Manual (Springer Verlag, Heidelberg/New York, 2000). Further related protocols are also available in Current Protocols in Immunology (August 2009,) published by John Wiley & Sons, Inc., Boston, Mass. Methods for production of enzymes and protein engineering (e.g., IDUA) are also known in the art and contemplated for use herein.

Thus, this disclosure provides polynucleotides (isolated or purified or pure polynucleotides) encoding the proteins of interest of this disclosure for genetically modifying B cells, vectors (including cloning vectors and expression vectors) comprising such polynucleotides, and cells (e.g., host cells) transformed or transfected with a polynucleotide or vector according to this disclosure. In certain embodiments, a polynucleotide (DNA or RNA) encoding a protein of interest of this disclosure is contemplated. Expression cassettes encoding proteins of interest are also contemplated herein.

The present disclosure also relates to vectors that include a polynucleotide of this disclosure and, in particular, to recombinant expression constructs. In one embodiment, this disclosure contemplates a vector comprising a polynucleotide encoding a protein of this disclosure, along with other polynucleotide sequences that cause or facilitate transcription, translation, and processing of such a protein-encoding sequences. Appropriate cloning and expression vectors for use with prokaryotic and eukaryotic hosts are described, for example, in Sambrook et ai, Molecular Cloning: A Laboratory Manual, Second Edition, Cold Spring Harbor, NY, (1989). Exemplary cloning/expression vectors include cloning vectors, shuttle vectors, and expression constructs, that may be based on plasmids, phagemids, phasmids, cosmids, viruses, artificial chromosomes, or any nucleic acid vehicle known in the art suitable for amplification, transfer, and/or expression of a polynucleotide contained therein.

As used herein, unless as otherwise described with regard to viral vectors, "vector" means a nucleic acid molecule capable of transporting another nucleic acid to which it has been linked. Exemplary vectors include plasmids, yeast artificial chromosomes, and viral genomes. Certain vectors can autonomously replicate in a host cell, while other vectors can be integrated into the genome of a host cell and thereby are replicated with the host genome. In addition, certain vectors are referred to herein as "recombinant expression vectors" (or simply, "expression vectors"), which contain nucleic acid sequences that are operatively linked to an expression control sequence and, therefore, are capable of directing the expression of those sequences. In certain embodiments, expression constructs are derived from plasmid vectors. Illustrative constructs include modified pNASS vector (Clontech, Palo Alto, Calif.), which has nucleic acid sequences encoding an ampicillin resistance gene, a polyadenylation signal and a T7 promoter site; pDEF38 and pNEF38 (CMC ICOS Biologies, Inc.), which have a CHEF1 promoter; and pD18 (Lonza), which has a CMV promoter. Other suitable mammalian expression vectors are well known (see, e.g., Ausubel et al., 1995; Sambrook et al., supra; see also, e.g., catalogs from Invitrogen, San Diego, Calif.; Novagen, Madison, Wis.; Pharmacia, Piscataway, N.J.). Useful constructs may be prepared that include a dihydrofolate reductase (DHFR)-encoding sequence under suitable regulatory control, for promoting enhanced production levels of the fusion proteins, which levels result from gene amplification following application of an appropriate selection agent (e.g., methotrexate).

Generally, recombinant expression vectors will include origins of replication and selectable markers permitting transformation of the host cell, and a promoter derived from a highly-expressed gene to direct transcription of a downstream structural sequence, as described above. A vector in operable linkage with a polynucleotide according to this disclosure yields a cloning or expression construct. Exemplary cloning/expression constructs contain at least one expression control element, e.g., a promoter, operably linked to a polynucleotide of this disclosure. Additional expression control elements, such as enhancers, factor-specific binding sites, terminators, and ribosome binding sites are also contemplated in the vectors and cloning/expression constructs according to this disclosure. The heterologous structural sequence of the polynucleotide according to this disclosure is assembled in appropriate phase with translation initiation and termination sequences. Thus, for example, encoding nucleic acids as provided herein may be included in any one of a variety of expression vector constructs as a recombinant expression construct for expressing such a protein in a host cell.

The appropriate DNA sequence(s) may be inserted into a vector, for example, by a variety of procedures. In general, a DNA sequence is inserted into an appropriate restriction endonuclease cleavage site(s) by procedures known in the art. Standard techniques for cloning, DNA isolation, amplification and purification, for enzymatic reactions involving DNA ligase, DNA polymerase, restriction endonucleases and the like, and various separation techniques are contemplated. A number of standard techniques are described, for example, in Ausubel et al. (Current Protocols in Molecular Biology, Greene Publ. Assoc. Inc. & John Wiley & Sons, Inc., Boston, Mass., 1993); Sambrook et al. (Molecular Cloning, Second Ed., Cold Spring Harbor Laboratory, Plainview, N.Y., 1989); Maniatis et al. (Molecular Cloning, Cold Spring Harbor Laboratory, Plainview, N.Y., 1982); Glover (Ed.) (DNA Cloning Vol. I and II, IRL Press, Oxford, UK, 1985); Hames and Higgins (Eds.) (Nucleic Acid Hybridization, IRL Press, Oxford, UK, 1985); and elsewhere.

The DNA sequence in the expression vector is operatively linked to at least one appropriate expression control sequence (e.g., a constitutive promoter or a regulated promoter) to direct mRNA synthesis. Representative examples of such expression control sequences include promoters of eukaryotic cells or their viruses, as described above. Promoter regions can be selected from any desired gene using CAT (chloramphenicol transferase) vectors or other vectors with selectable markers. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a nucleic acid encoding a protein or polypeptide according to this disclosure is described herein.

Variants of the polynucleotides of this disclosure are also contemplated. Variant polynucleotides are at least 60%, 65%, 70%, 75%, 80%, 85%, 90%, and preferably 95%, 96%, 97%, 98%, 99%, or 99.9% identical to one of the polynucleotides of defined sequence as described herein, or that hybridizes to one of those polynucleotides of defined sequence under stringent hybridization conditions of 0.015M sodium chloride, 0.0015M sodium citrate at about 65-68[deg.]C or 0.015M sodium chloride, 0.0015M sodium citrate, and 50% formamide at about 42[deg.]C. The polynucleotide variants retain the capacity to encode a binding domain or fusion protein thereof having the functionality described herein.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015M sodium chloride, 0.0015M sodium citrate at about 65-68[deg.]C or 0.015M sodium chloride, 0.0015M sodium citrate, and 50% formamide at about 42[deg.]C (see Sambrook et ai, Molecular Cloning: A Laboratory Manual, 2nd Ed., Cold Spring Harbor Laboratory, Cold Spring Harbor, N.Y., 1989). More stringent conditions (such as higher temperature, lower ionic strength, higher formamide, or other denaturing agent) may also be used; however, the rate of hybridization will be affected. In instances wherein hybridization of deoxyoligonucleotides is concerned, additional exemplary stringent hybridization conditions include washing in 6×SSC, 0.05% sodium pyrophosphate at 37[deg.]C (for 14-base oligonucleotides), 48[deg.]C (for 17-base oligonucleotides), 55[deg.]C (for 20-base oligonucleotides), and 60[deg.]C (for 23-base oligonucleotides).

A further aspect of this disclosure provides a host cell transformed or transfected with, or otherwise containing, any of the polynucleotides or vector/expression constructs of this disclosure. The polynucleotides or cloning/expression constructs of this disclosure are introduced into suitable cells using any method known in the art, including transformation, transfection and transduction. Host cells include the cells of a subject undergoing ex vivo cell therapy including, for example, ex vivo gene therapy. Eukaryotic host cells contemplated as an aspect of this disclosure when harboring a polynucleotide, vector, or protein according to this disclosure include, in addition to a subject's own cells (e.g., a human patient's own cells), VERO cells, HeLa cells, Chinese hamster ovary (CHO) cell lines (including modified CHO cells capable of modifying the glycosylation pattern of expressed multivalent binding molecules, see US Patent Application Publication No. 2003/01 15614), COS cells (such as COS-7), W138, BHK, HepG2, 3T3, RIN, MDCK, A549, PC12, K562, HEK293 cells, HepG2 cells, N cells, 3T3 cells, *Spodoptera frugiperda* cells (e.g., Sf9 cells), *Saccharomyces cerevisiae* cells, and any other eukaryotic cell known in the art to be useful in expressing, and optionally isolating, a protein or peptide according to this disclosure. Also contemplated are prokaryotic cells, including *Escherichia coli, Bacillus subtilis, Salmonella typhimurium*, a Streptomycete, or any prokaryotic cell known in the art to be suitable for expressing, and optionally isolating, a protein or peptide according to this disclosure. In isolating protein or peptide from prokaryotic cells, in particular, it is contemplated that techniques known in the art for extracting protein from inclusion bodies may be used. The selection of an appropriate host is within the scope of those skilled in the art from the teachings herein. Host cells that glycosylate the fusion proteins of this disclosure are contemplated.

The term "recombinant host cell" (or simply "host cell") refers to a cell containing a recombinant expression vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells can be cultured in a conventional nutrient medium modified as appropriate for activating promoters, selecting transformants, or amplifying particular genes. The culture conditions for particular host cells selected for expression, such as temperature, pH and the like, will be readily apparent to the ordinarily skilled artisan. Various mammalian cell culture systems can also be employed to express recombinant protein. Examples of mammalian expression systems include the COS-7 lines of monkey kidney fibroblasts, described by Gluzman (1981) Cell 23:175, and other cell lines capable of expressing a compatible vector, for example, the C127, 3T3, CHO, HeLa and BHK cell lines. Mammalian expression vectors will comprise an origin of replication, a suitable promoter and, optionally, enhancer, and also any necessary ribosome binding sites, polyadenylation site, splice donor and acceptor sites, transcriptional termination sequences, and 5'-flanking nontranscribed sequences, for example, as described herein regarding the preparation of multivalent binding protein expression constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including calcium phosphate transfection, DEAE-Dextran-mediated transfection, or electroporation (Davis et al. (1986) Basic Methods in Molecular Biology).

Compositions and Methods of Use

In one embodiment, the cell compositions of the present disclosure comprise B cell which has been activated/differentiated in vitro and transduced to express a protein of interest as described herein. In one embodiment, the compositions comprise B cells that have differentiated into plasma B cells, have been transduced and express one or more proteins of interest. Target cell populations, such as the transduced and activated B cell populations of the present disclosure may be administered either alone, or as a pharmaceutical composition in combination with diluents and/or with other components such as cytokines or cell populations. Briefly, cell compositions of the present disclosure may comprise a differentiated and activated B cell population that has been transduced and is expressing a protein of interest as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

Cell compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an effective amount", "an anti-tumor effective amount", "a tumor-inhibiting effective amount", or "therapeutic amount" is indicated, the precise amount of the compositions of the present disclosure to be administered can be determined by a physician with consideration of individual differences in age, weight, tumor size, extent of infection or metastasis, and condition of the patient (subject). B cell compositions may also be administered multiple times at an appropriate dosage(s). The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly. Typically, in related adoptive immunotherapy studies, antigen-specific T cells are administered approximately at $2 \times 10^9$ to $2 \times 10^{11}$ cells to the patient. (See, e.g., U.S. Pat. No. 5,057,423). In some aspects of the present disclosure, lower numbers of the transduced B cells of the present disclosure, in the range of $10^6$/kilogram ($10^6$-$10^{11}$ per patient) may be administered. In certain embodiments, the B cells are administered at $1 \times 10^5$, $1 \times 10^6$, $1 \times 10^7$, $1 \times 10^8$, $2 \times 10^8$, $2 \times 10^9$, $1 \times 10^{10}$, $2 \times 10^{10}$, $1 \times 10^{11}$, $5 \times 10^{11}$, or $1 \times 10^{12}$ cells to the subject. B cell compositions may be administered multiple times at dosages within these ranges. The cells may be autologous or heterologous to the patient undergoing therapy. If desired, the treatment may also include administration of mitogens (e.g., PHA) or lymphokines, cytokines, and/or chemokines (e.g., GM-CSF, IL-4, IL-13, Flt3-L, RANTES, MIP1 a, etc.) as described herein to enhance induction of an immune response.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the B cell compositions of the present disclosure are administered to a patient by intradermal or subcutaneous injection. In another embodiment, the B cell compositions as described herein are preferably administered by i.v. injection. The compositions of B cells may be injected directly into a tumor, lymph node, bone marrow or site of infection.

In yet another embodiment, the pharmaceutical composition can be delivered in a controlled release system. In one embodiment, a pump may be used (see Langer, 1990, Science 249:1527-1533; Sefton 1987, CRC Crit. Ref. Biomed. Eng. 14:201; Buchwald et al., 1980; Surgery 88:507; Saudek et al., 1989, N. Engl. J. Med. 321:574). In another embodiment, polymeric materials can be used (see Medical Applications of Controlled Release, 1974, Langer and Wise (eds.), CRC Pres., Boca Raton, Fla.; Controlled Drug Bioavailability, Drug Product Design and Performance, 1984, Smolen and Ball (eds.), Wiley, New York; Ranger and Peppas, 1983; J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, thus requiring only a fraction of the systemic dose (see, e.g., Medical Applications of Controlled Release, 1984, Langer and Wise (eds.), CRC Pres., Boca Raton, Fla., vol. 2, pp. 1 15-138).

The B cell compositions of the present disclosure may also be administered using any number of matrices. Matrices have been utilized for a number of years within the context of tissue engineering (see, e.g., Principles of Tissue Engineering (Lanza, Langer, and Chick (eds.)), 1997. The present disclosure utilizes such matrices within the novel context of acting as an artificial lymphoid organ to support and maintain the B cells. Accordingly, the present disclosure can utilize those matrix compositions and formulations which have demonstrated utility in tissue engineering. Accordingly, the type of matrix that may be used in the compositions, devices and methods of the disclosure is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized. Matrices comprise features commonly associated with being biocompatible when administered to a mammalian host. Matrices may be formed from both natural or synthetic materials. The matrices may be nonbiodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release seeded cells or produced cytokine or other active agent. In certain embodiments, the matrix of the present disclosure is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current disclosure is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

In certain embodiments of the present disclosure, B cells transduced and activated using the methods described herein, or other methods known in the art, are administered to a patient in conjunction with (e.g. before, simultaneously or following) any number of relevant treatment modalities, including but not limited to treatment with agents such as antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993; Isoniemi (supra)). In a further embodiment, the cell compositions of the present disclosure are administered to a patient in conjunction with (e.g. before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In one embodiment, the cell compositions of the present disclosure are administered following B-cell ablative therapy such as agents that react with CD20, e.g. Rituxan®. For example, in one embodiment, subjects may undergo standard treatment with high dose chemotherapy followed by peripheral blood stem cell transplantation. In certain embodiments, following the transplant, subjects receive an infusion of the expanded immune cells of the present disclosure. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices.

The transduced B cell compositions of the disclosure, particularly B cells transduced to express a particular antibody of interest, can be used in the treatment or prevention of various infectious diseases, cancers, degenerative diseases and immunological disorders.

Compositions comprising the transduced B cells as described herein may be used in treatment of any of a variety of infectious diseases caused by infectious organisms, such as viruses, bacteria, parasites and fungi. Infectious organisms may comprise viruses, (e.g., RNA viruses, DNA viruses, human immunodeficiency virus (HIV), hepatitis A, B, and C virus, herpes simplex virus (HSV), cytomegalovirus (CMV) Epstein-Barr virus (EBV), human papilloma virus (HPV)), parasites (e.g., protozoan and metazoan pathogens such as *Plasmodia* species, *Leishmania* species, *Schistosoma* species, *Trypanosoma* species), bacteria (e.g., Mycobacteria, in particular, *M. tuberculosis*, *Salmonella*, *Streptococci*, *E. coli*, *Staphylococci*), fungi (e.g., *Candida* species, *Aspergillus* species), *Pneumocystis carinii*, and prions (known prions infect animals to cause scrapie, a transmissible, degenerative disease of the nervous system of sheep and goats, as well as bovine spongiform encephalopathy (BSE), or "mad cow disease", and feline spongiform encephalopathy of cats. Four prion diseases known to affect humans are (1) kuru, (2) Creutzfeldt-Jakob Disease (CJD), (3) Gerstmann-Straussler-Scheinker Disease (GSS), and (4) fatal familial insomnia (FFI)). As used herein "prion" includes all forms of prions causing all or any of these diseases or others in any animals used-and in particular in humans and domesticated farm animals. Illustrative infectious diseases include, but are not limited to, toxoplasmosis, histoplasmosis, CMV, EBV, coccidiomycosis, tuberculosis, HIV, and the like.

In certain embodiments, the transduced B cell compositions as described herein may also be used for the prevention or treatment of a variety of cancers. In this regard, in certain embodiments, the compositions comprising transduced B cells are useful for preventing or treating melanoma, non-Hodgkin's lymphoma, Hodgkin's disease, leukemia, plasmocytoma, sarcoma, glioma, thymoma, breast cancer, prostate cancer, colo-rectal cancer, kidney cancer, renal cell carcinoma, uterine cancer, pancreatic cancer, esophageal cancer, brain cancer, lung cancer, ovarian cancer, cervical cancer, testicular cancer, gastric cancer, esophageal cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers.

In one embodiment, the transduced B cells may also be used in the treatment of immunological disorders such as acquired immune deficiency syndrome (AIDS), agammaglobulinemia, hypogammaglobulinemia, other immunodeficiencies, immunosuppression, and severe combined immunodeficiency disease (SCID).

In one embodiment, the transduced B cells as described herein may also be used in the treatment of autoimmune diseases such as, but not limited to, rheumatoid arthritis, multiple sclerosis, insulin dependent diabetes, Addison's disease, celiac disease, chronic fatigue syndrome, inflammatory bowel disease, ulcerative colitis, Crohn's disease, Fibromyalgia, systemic lupus erythematosus, psoriasis, Sjogren's syndrome, hyperthyroid ism/Graves disease, hypothyroidism/Hashimoto's disease, Insulin-dependent diabetes (type 1), Myasthenia Gravis, endometriosis, scleroderma, pernicious anemia, Goodpasture syndrome, Wegener's disease, glomerulonephritis, aplastic anemia, paroxysmal nocturnal hemoglobinuria, myelodysplastic syndrome, idiopathic thrombocytopenic purpura, autoimmune hemolytic anemia, Evan's syndrome, Factor VIII inhibitor syndrome, systemic vasculitis, dermatomyositis, polymyositis and rheumatic fever. Thus, in one embodiment, the methods herein include methods for treating a disease comprising administering to a subject or patient in need thereof a therapeutically effective amount of the compositions comprising the transduced B cells as described herein, thereby treating the disease.

EXAMPLES

Example 1

In Vitro Memory B Cell Differentiation and Transduction with VSV-G Pseudotyped Lentivirus This Example describes the in vitro differentiation of plasmablasts and plasma cells and transduction of same with VSV-G virus. The present methods demonstrate that after the 2nd phase of the culture system, about 20% transduction is observed as compared to only 5% using methods known in the art.

(For the transduction: No spinnoculation, just add viral supernant with protamine sulfate and incubate for overnight, change medium)

Memory B cells were isolated using the memory B cell isolation protocol described below.
1. D1: resuspend purified memory B cell into 1.5E5/ml medium #1, supplemented with combination of cytokines, incubate for 3 days.
2. D4: cells were harvested, washed with base medium, spin down at 300 g for 8 mins, and resuspend cells in medium #2, supplemented with combination of cytokines.
3. D6: Cells were collected and counted, resuspend cells at 1.5E6/ml in medium #2, add protamine sulfate (100×) 10 ul+concentrated GFP virus 100 ul (~MOI 50), incubate overnight.
4. D7: cells were harvested, washed with base medium, spin down at 300 g for 8 mins, and resuspend in medium #3, supplemented with combination of cytokines, incubate for 3 days.
5. D10: Collect cells by spinning down at 300 g for 8 mins, and fix cells in fixation buffer for 15 mins at 4 C. Wash cells twice and keep them in flow buffer. They are ready for flow analysis to determine transduction efficiency.

The cells after the 2nd step are mostly CD20−, CD38+, CD138− and after the 3rd step CD20−, CD38+, CD138+.

| Medium: Base Medium | | |
|---|---|---|
| IMDM medium | | 405 ml |
| 10% FBS | | 45 ml |
| 1% P/S | | 4.5 ml |
| 50 ug/ml human transferrin (1000×) | | 450 ul |
| 5 ug/ml human insulin (1000×) | | 450 ul |
| Medium #1 for D1-: | Stock | For 15 ml |
| 50 ng/ml His-tagged CD40L | 50 ug/ml (1000×) | 15 ul |
| 5 ug/ml Anti-poly-his mAb | 500 ug/ml (100×) | 150 ul |
| 20 U/ml IL-2 | 5.7E5 u/ml (2850×) | 5.25 ul |
| 50 ng/ml IL-10 | 100 ug/ml (2000×) | 7.5 ul |
| 10 ng/ml IL-15 | 10 ug/ml (1000×) | 15 ul |
| 10 ug/ml p-ODN | 10 mg/ml (1000×) | 15 ul |
| Medium #2 for D4-: | | For 15 ml |
| 20 U/ml IL-2 | 5.7E5 u/ml (2850×) | 5.25 ul |
| 50 ng/ml IL-10 | 100 ug/ml (2000×) | 7.5 ul |
| 50 ng/ml IL-6 | 50 ug/ml (1000×) | 15 ul |
| 10 ng/ml IL-15 | 10 ug/ml (1000×) | 15 ul |
| Medium #3 for D7-: | | For 15 ml |
| 500 U/ml IFN-A/D | 1E6 u/ml (2000×) | 7.5 ul |
| 50 ng/ml IL-6 | 50 ug/ml (1000×) | 15 ul |
| 10 ng/ml IL-15 | 10 ug/ml (1000×) | 15 ul |

Stock Reagent Preparation:
1. Insulin 50 mg (Sigma) was dissolved in 0.005N HCL, filtered (0.22 um) and aliquoted at 1 ml/tube, stored at −20° C. Stock conc is 5 mg/ml (1000×)
2. Transferrin 100 mg (Sigma) was dissolved in 2 ml PBS, filtered (0.22 um) and aliquoted at 0.5 ml/tube, stored at −20° C. Stock conc is 50 mg/ml (1000×)
3. P-ODN 47.95 mg (IDT synthesized) was dissolved in 4.795 ml sterile ddH2O, aliquoted at 1 ml/tube, stored at −20° C. Stock conc is 10 mg/ml (1000×)
4. sCD40L-his (20 ug/40 ul) (Prospec) was diluted into sterile 0.4 ml PBS/0.5% BSA, and aliquoted at 130 ul/tube, stored at −20° C. Stock conc is 50 ug/ml (1000×)
5. IL15 5 ug (R&D) was dissolved in 0.5 ml sterile PBS/0.5% BSA, aliquoted at 100 ul/tube, stored at −20° C. Stock conc is 10 ug/ml (1000×)
6. IL6 10 ug (R&D) was dissolved in 0.2 ml sterile PBS/0.5% BSA, aliquoted at 50 ul/tube, stored at −20° C. Stock conc is 50 ug/ml (1000×)
7. IL2 (eBioscience) was 100 ug/ml, 5.6E6 u/mg. So it is 5.7E5 u/ml (2850×)
8. IL 10 (eBioscience) was 100 ug/ml (2000×)
9. IFN 0.1 ml total for 100000 U. The stock conc is 1E6 u/ml (2000×)
10. Anti-poly his antibody.

The majority of the starting population in the above method is CD20+, CD38−, CD138− and they transduce poorly. The cells after the 2nd step are mostly CD20−, CD38+, CD138− and after the 3rd step CD20−, CD38+, CD138+. No methods described in the art have used differentiation of plasmablasts and plasma cells in vitro and combined with VSV-G transduction. Using this in vitro method, transduction efficiency was greatly increased, to about 20%.

Figure 2:
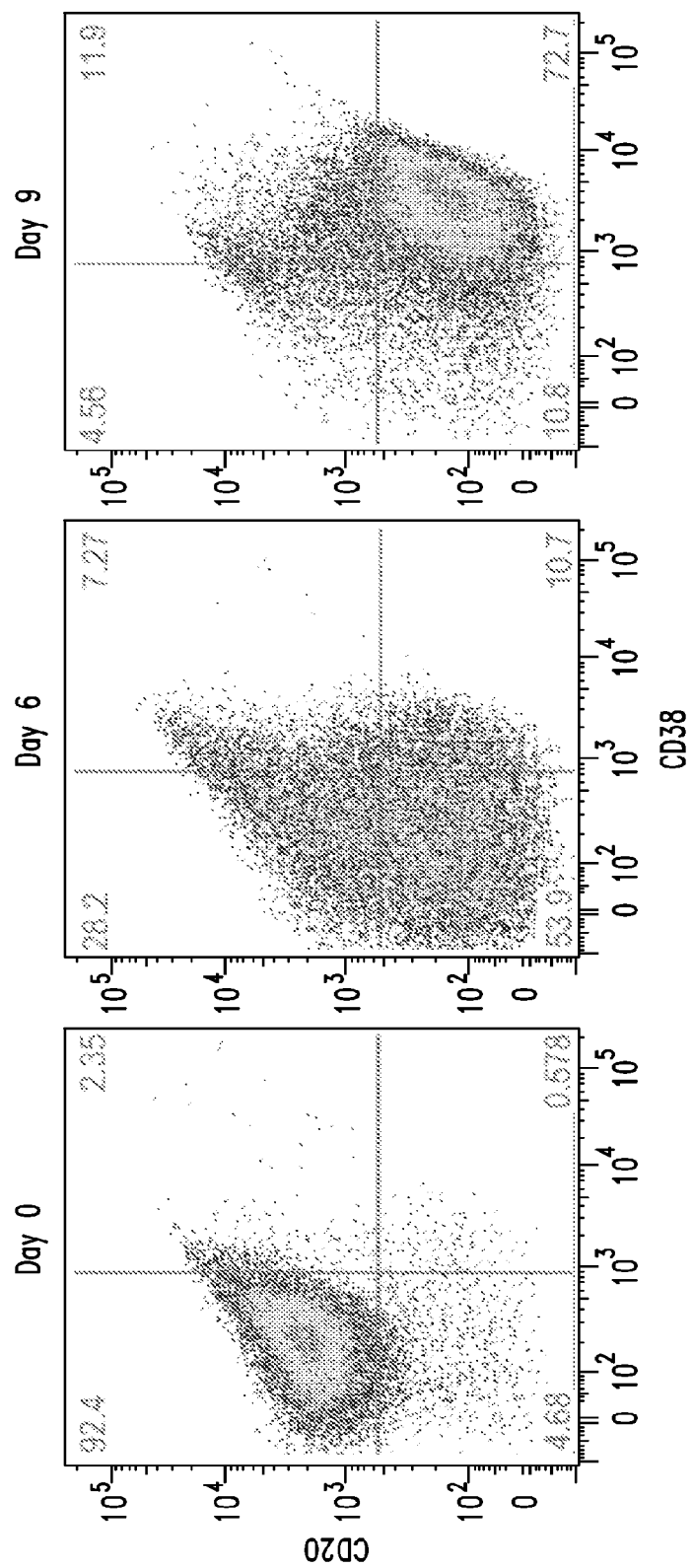
FIG. 2 is a series of flow cytometry dot plots that show memory B cell differentiation over 9 days of in vitro culture. CD20 is shown on the y-axis, and CD38 is shown on the x-axis.

In particular, the culture conditions demonstrated herein for the first time generated a window of time during which the B cells were amenable to transduction (FIG. 1). Efficient transduction of B cells with the VSV-G psuedotyped virus required conditions that stimulated both B cell proliferation and result in a specific B cell phenotype. The variations in the CD20+; CD38−, CD20−; CD38−, CD20−; and CD38+ phenotypes over the course of 9 days in culture are shown in FIG. 2.

Figure 3:
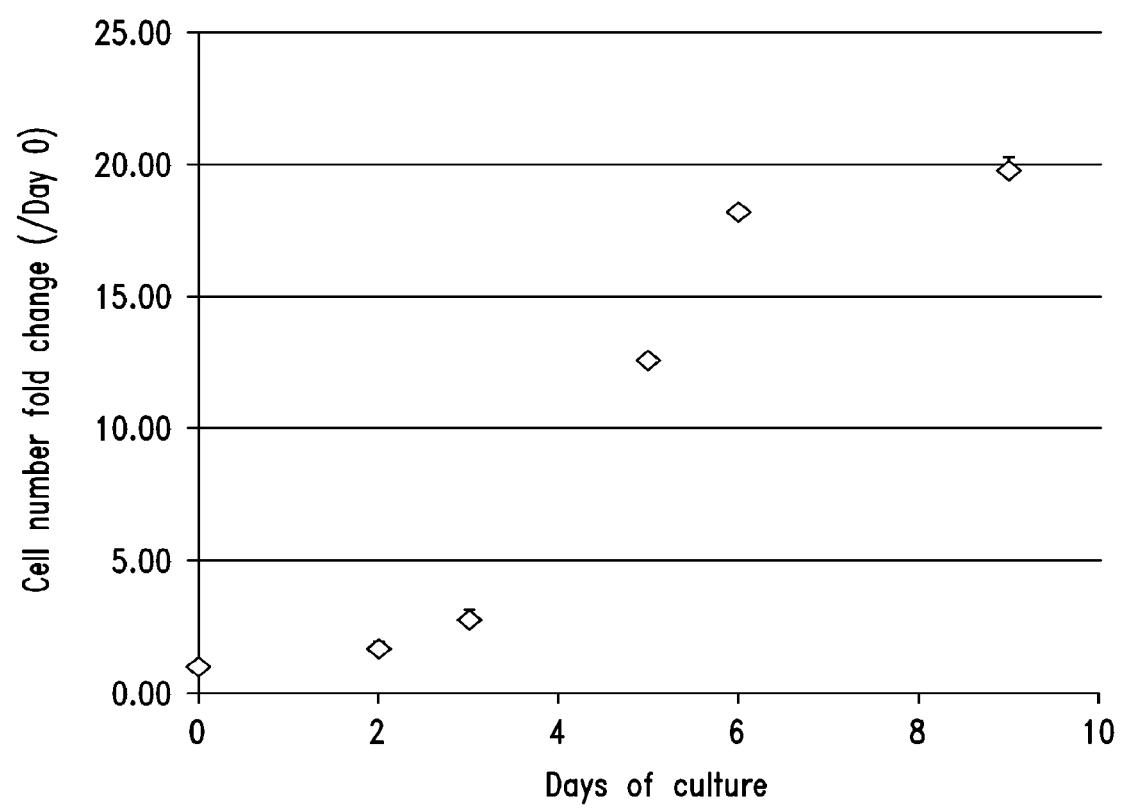
FIG. 3 is a dot plot that shows cell growth during 9 days of in vitro culture. The fold change in cell number relative to the number of cells present on Day 0 is provided on the y-axis, and the number of days in culture is provided along the x-axis.

As shown in FIG. 1, after 5 days in culture designed to promote B cell differentiation, the cells became maximally amenable to transduction. The timing of the B cells transitioning phenotypically also correlated to the cells being in a maximally proliferative state (FIG. 3). The culture conditions induced cell proliferation and phenotypic transition that resulted in transduction efficiency significantly greater than what has been observed using other methods. Accordingly, the present methods can be used to efficiently transduce B cells to express a protein of interest, such as a specific antibody or other therapeutic protein.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An in vitro culture method for expressing a nucleic acid of interest in B cells comprising,
   (a) contacting B cells that are CD20+,CD38−, and CD138− with a composition comprising multimerized soluble CD40L in combination with IL-2, IL-10, IL-15, and CpG oligodeoxynucleotides (p-ODN) until the B cells become CD20−, CD38−, CD138−, and CD27+;
   (b) removing the composition comprising multimerized soluble CD40L in combination with IL-2, IL-10, IL-15, and CpG oligodeoxynucleotides (p-ODN) from the B cells and contacting the remaining B cells with IL-2, IL-10, IL-6 and IL-15 until the B cells are mostly CD20−, CD38+, and CD138−; and
   (c) transducing the B cells after step (b) on day 5 after the start of in vitro culture with a retroviral vector pseudotyped with VSV-G, wherein said retroviral vector comprises the nucleic acid of interest operably linked to a promoter, wherein the transduction efficiency is about 20%, thereby expressing the nucleic acid of interest in B cells.

2. The method of claim 1, wherein the CD40L is sCD40L-his.

3. The method of claim 1, wherein the retroviral vector is a lentiviral vector.

4. The method of claim 1 wherein the nucleic acid of interest comprises a nucleic acid encoding at least an immunoglobulin VL and VH region.

5. The method of claim 1 wherein the nucleic acid of interest encodes an antibody protein, or antigen-binding fragment thereof, a fusion protein or a DNA-encoded small molecule.

6. The method of claim 5 wherein the antibody is an anti-HIV antibody, an anti-RNA antibody, or an antibody that binds a protein involved in immune regulation.

7. The method of claim 1 wherein the B cells are isolated from peripheral blood.

8. The method of claim 1, further comprises removing transduced B cells of (c) expressing CD38 and CD138 and contacting the transduced B cells of (c) expressing CD38 and CD138 with IFN-α, IFN-δ, IL-6 and IL-15.

9. An in vitro culture method for expressing a nucleic acid of interest in B cells comprising,
   (a) contacting a B cell population comprising memory B cells with a composition comprising multimerized soluble CD40L in combination with IL-2, IL-10, IL-15, and CpG oligodeoxynucleotides (p-ODN) for about 3 days;
   (b) removing the composition comprising multimerized soluble CD40L in combination with IL-2, IL-10, IL-15, and CpG oligodeoxynucleotides (p-ODN) from the B cells and contacting the remaining B cells with IL-2, IL-10, IL-6 and IL-15, under conditions such that the B cells express CD38; and
   (c) transducing the B cells after step (b) on day 5 after the start of in vitro culture with a retroviral vector pseudotyped with VSV-G, wherein said retroviral vector comprises the nucleic acid of interest operably linked to a promoter,
   thereby expressing the nucleic acid of interest in B cells, wherein transduction efficiency is about 20%.

10. The method of claim 9, further comprises removing transduced B cells of (c) expressing CD38 and CD138 and contacting the transduced B cell of (c) expressing CD38 and CD138 with IFN-α, IFN-δ, IL-6 and IL-15.

11. The method of claim 9, wherein the CD40L is sCD40L-his.

12. The method of claim 9 wherein the retroviral vector is a lentiviral vector.

13. The method of claim 9 wherein the nucleic acid of interest comprises a nucleic acid encoding at least an immunoglobulin VL and VH region.

14. The method of claim 9 wherein the nucleic acid of interest encodes an antibody protein, or antigen-binding fragment thereof, a fusion protein or a DNA-encoded small molecule.

15. The method of claim 14 wherein the antibody is an anti-HIV antibody, an anti-RNA antibody, or an antibody that binds a protein involved in immune regulation.

16. The method of claim 9 wherein the memory B cells are isolated from peripheral blood.

17. The method of claim 9 wherein the B cells of (b) are CD20−, CD38+ and CD138−.

18. The method of claim 9 wherein the B cells of (c) are CD20−, CD38+ and CD138+.

* * * * *